US012685878B2

(12) United States Patent
Fishman et al.

(10) Patent No.: US 12,685,878 B2
(45) Date of Patent: Jul. 21, 2026

(54) INTENSITY AND DOSE MODULATED RADIOSURGICAL NEEDLE SYSTEM AND METHOD

(71) Applicant: Empyrean Medical Systems, Inc., Boca Raton, FL (US)

(72) Inventors: Kalman Fishman, Boca Raton, FL (US); Dirk Bartkoski, Knoxville, TN (US); Jacob Scott, Gates Mills, OH (US)

(73) Assignee: EMPYREAN MEDICAL SYSTEMS, INC., Boca Raton, FL (US)

( * ) Notice: Subject to any disclaimer, the term of this patent is extended or adjusted under 35 U.S.C. 154(b) by 0 days.

(21) Appl. No.: 18/944,949

(22) Filed: Nov. 12, 2024

(65) Prior Publication Data

US 2025/0152970 A1     May 15, 2025

Related U.S. Application Data

(60) Provisional application No. 63/597,882, filed on Nov. 10, 2023.

(51) Int. Cl.
A61N 5/10 (2006.01)

(52) U.S. Cl.
CPC ......... A61N 5/1007 (2013.01); A61N 5/1049 (2013.01); A61N 5/1083 (2013.01); A61N 2005/1008 (2013.01); A61N 5/1017 (2013.01); A61N 2005/1022 (2013.01); A61N 2005/1058 (2013.01); A61N 2005/1085 (2013.01)

(58) Field of Classification Search
None
See application file for complete search history.

(56) References Cited

U.S. PATENT DOCUMENTS

| | | | | |
|---|---|---|---|---|
| 5,369,679 | A * | 11/1994 | Sliski | H05G 1/10 |
| | | | | 378/65 |
| 6,241,670 | B1 * | 6/2001 | Nambu | A61N 5/1048 |
| | | | | 378/65 |
| 10,413,755 | B1 | 9/2019 | Sahadevan | |
| 2005/0226378 | A1 * | 10/2005 | Cocks | H01J 35/32 |
| | | | | 378/65 |
| 2006/0067467 | A1 * | 3/2006 | Chornenky | A61N 5/1015 |
| | | | | 378/65 |
| 2019/0060674 | A1 | 2/2019 | Fishman | |
| 2023/0178324 | A1 | 6/2023 | Fishman et al. | |

OTHER PUBLICATIONS

International Search Report and Written Opinion mailed on Jan. 15, 2025 in PCT/US24/55491.

* cited by examiner

*Primary Examiner* — Hoon K Song
(74) *Attorney, Agent, or Firm* — FOX ROTHSCHILD LLP

(57)     ABSTRACT

A radiotherapy device includes an electron source, a first beam corrector, a drift tube, a target with target material that when impacted by an electron beam generates Bremsstrahlung x-ray photons, and a radiosurgical needle. The radiosurgical needle has an elongated radiopaque needle body with a lumen and a pointed tip for piercing a tissue of a patient. The target is positioned within the lumen of the radiosurgical needle. A first beam steering device steers a focused electron beam within the micro drift tube to the target. A radiotherapy system and a method for conducting radiotherapy are also disclosed.

36 Claims, 25 Drawing Sheets

INTENSITY AND DOSE MODULATED RADIOSURGICAL NEEDLE SYSTEM AND METHOD

CROSS-REFERENCE TO RELATED APPLICATIONS

This application claims priority to U.S. 63/597,882 filed on Nov. 10, 2023, entitled "INTENSITY AND DOSE MODULATED RADIOSURGICAL NEEDLE SYSTEM AND METHOD", the entire disclosure of which incorporated herein by reference.

FIELD OF THE INVENTION

The present invention relates generally to radiation therapy, and more particularly to systems and methods for performing radiation therapy using x-ray photons.

BACKGROUND OF THE INVENTION

One of the most common forms of brachytherapy are forms of internal radiation therapy where radioactive material is placed inside or next to a tumor. Internal radiation therapy utilizes radioactive material sealed inside a seed, pellet, wire, or capsule that is implanted in the body using a needle or catheter and remains in the body. The radiation emitted by the radioactive material damages the DNA of cancer cells within a tumor. A common indication for such internal radiation therapy procedures is prostate cancer.

Another form of radiation therapy is the external beam radiation therapy (EBRT), in which high-energy x-ray beams are generated outside the body and aimed at a tumor inside the body. External beam radiation sources can be used to generate photons, protons or electrons, and utilize guidance systems to direct the beam to the proper location within the patient's body. Such devices include proton therapy machines, linear accelerators (LINAC), and x-ray orthovoltage, among others.

The advantage of EBRT devices and methods is that there is no surgical penetration of the skin. In intra-operative radiation therapy (IORT), the radiation is projected through a surgical opening. IORT delivers a localized dose with a source that is positioned at or very near the tumor site, however, these procedures are inherently more invasive. Accordingly, both methods have disadvantages.

SUMMARY OF THE INVENTION

A radiotherapy system includes an electron source for generating an initial electron beam. A first beam corrector for focuses the initial electron beam into a focused electron beam. A target comprises target material that when impacted by the focused electron beam generates Bremsstrahlung x-ray photons. A radiosurgical needle has an elongated radiopaque needle body portion having an interior lumen, a proximal end and a distal end. The distal end comprises a pointed tip for piercing a tissue of a patient. The target is positioned within the lumen of the radiosurgical needle and closer to the distal end than the proximal end.

An elongated radiopaque micro drift tube has an open interior extending from the electron source to the radiosurgical needle. The micro drift tube has a proximal end nearest the electron source, and a distal end nearest the radiosurgical needle. The proximal end of the radiosurgical needle is affixed to the distal end of the micro drift tube. The open interior of the micro drift tube communicates with the lumen of the radiosurgical needle so as to define an electron flow path from the electron source to the target. A first beam steering device steers the focused electron beam within the micro drift tube to the target. The distal end of the radiosurgical needle can include a radiolucent portion for transmitting x-ray photons generated at the target.

The radiotherapy system can include a vacuum connection for connecting to a vacuum source for maintaining a vacuum within the open interior of the micro drift tube and the lumen of the radiosurgical needle.

The open interior of the micro drift tube can have a diameter of from 1 to 5 mm. The interior lumen of the radiosurgical needle can have a diameter of between 1 and 5 mm. The elongated radiopaque needle body portion of the radiosurgical needle can have an outside diameter of from 1 to 5 mm.

The pointed tip can include an open space defined by interior tip walls. The target material can be affixed to the interior tip walls. The open space of the pointed tip communicates with the lumen of the radiosurgical needle to permit the focused electron beam to strike the target material affixed to the interior tip walls.

The target material can be provided proximal to the pointed tip. The target material can span the lumen of the radiosurgical needle. The radiolucent portion of the radiosurgical needle can be provided in the pointed tip, wherein x-ray photons generated at the target material will be transmitted through the pointed tip. The radiolucent portion of the radiosurgical needle can be provided proximal to the target material so as to transmit x-ray photons proximal to the target material.

The target material can include at least one selected from the group consisting of molybdenum, tungsten and gold. The target material can be disposed on a substrate. The substrate can include at least one selected from the group consisting of beryllium, aluminum, sapphire, diamond, alumina, and boron nitride. The radiolucent portion can include silicon carbide.

The radiotherapy system can include a robotic support. The robotic support moves the radiosurgical needle to a treatment location within a patient, and for withdrawing the radiosurgical needle from the treatment location.

The radiotherapy system can further include a processor for receiving treatment planning data and patient position data. The processor processes the treatment planning data and the patient position data to move the radiosurgical needle to a treatment location within the patient and causes the electron source, the beam corrector and the beam steering device to direct the beam to a target with a beam energy and for a duration according to the treatment plan. The electron source, beam corrector, first beam steering device, micro drift tube, and radiosurgical needle can be provided in a treatment head. The treatment head can be connected to the robotic support. The robotic support can comprise a robotic arm capable of three-dimensional movement.

The radiotherapy system can further comprise a guidance module. The guidance module includes a guidance device. The guidance device has spatial orientation tags. The guidance module can include a guidance support for mounting the guidance device. The guidance module can include an ultrasound device which can be mounted to the guidance support. The guidance device can also include apertures dimensioned to receive the radiosurgical needle.

The radiotherapy system can include a second beam corrector. The second beam corrector is distal to the first beam corrector and the first beam steering device, and closer to the proximal end of the radiosurgical needle than the first beam corrector. The second beam corrector acts on the focused electron beam to produce a refocused electron beam at a distal end of the micro drift tube. The radiotherapy system can further include a second beam steering device. The second beam steering device is distal to the first beam corrector and the first beam steering device, and closer to the proximal end of the radiosurgical needle than the first beam steering device. The second beam steering device steers the refocused electron beam to the target.

A radiotherapy system includes a treatment head. The treatment head includes an electron source for generating an initial electron beam, a first beam corrector for focusing the initial electron beam into a focused electron beam, a target comprising target material that when impacted by the focused electron beam generates Bremsstrahlung x-ray photons, and a radiosurgical needle. The radiosurgical needle has an elongated radiopaque needle body portion having an interior lumen, a proximal end and a distal end. The distal end has a pointed tip. The target is positioned within the lumen and closer to the distal end than the proximal end. The distal end of the radiosurgical needle includes a radiolucent portion for transmitting x-ray photons generated at the target. The radiosurgical needle further comprises a pointed tip portion for piercing a tissue of a patient.

The treatment head further includes a first beam steering device for steering the focused electron beam to the target, and an elongated radiopaque micro drift tube with an open interior extending from the electron source to the radiosurgical needle. The micro drift tube has a proximal end nearest the electron source, and a distal end nearest the radiosurgical needle. The proximal end of the radiosurgical needle is affixed to the distal end of the micro drift tube. The open interior of the micro drift tube communicates with the lumen of the radiosurgical needle so as to define an electron flow path from the electron source to the target.

The radiotherapy system further includes a robotic arm for manipulating the treatment head. A base unit can be provided to support the robotic arm. The base unit can be mobile and provided on wheels and/or motorized.

A method for conducting radiotherapy can include the step of providing a radiosurgical needle with an elongated radiopaque needle body portion having an interior lumen, a proximal end and a distal end, the distal end comprising a pointed tip for piercing the tissue of a patient, the radiosurgical needle further comprising a target comprising target material that when impacted by the focused electron beam generates Bremsstrahlung x-ray photons, the target being positioned within the lumen and closer to the distal end than the proximal end, the distal end of the radiosurgical needle comprising a radiolucent portion for transmitting x-ray photons generated at the target.

The method further includes the step of inserting the radiosurgical needle into the body of a patient by piercing a tissue of the patient and advancing the radiosurgical needle to a patient therapy location. The method then directs a focused and steered electron beam at the target, wherein Bremsstrahlung x-ray photons will be generated at the target and will be transmitted through the radiolucent portion to the patient therapy location. The patient therapy location can be a tumor in a prostate. The patient therapy location can be a tumor in an eye. The patient therapy location can be a tumor of the spine. Many other patient therapy locations can be treated, for example, wherever solid tumors are located.

BRIEF DESCRIPTION OF THE DRAWINGS

There are shown in the drawings embodiments that are presently preferred it being understood that the invention is not limited to the arrangements and instrumentalities shown, wherein.

DETAILED DESCRIPTION OF THE INVENTION

Figure 1:
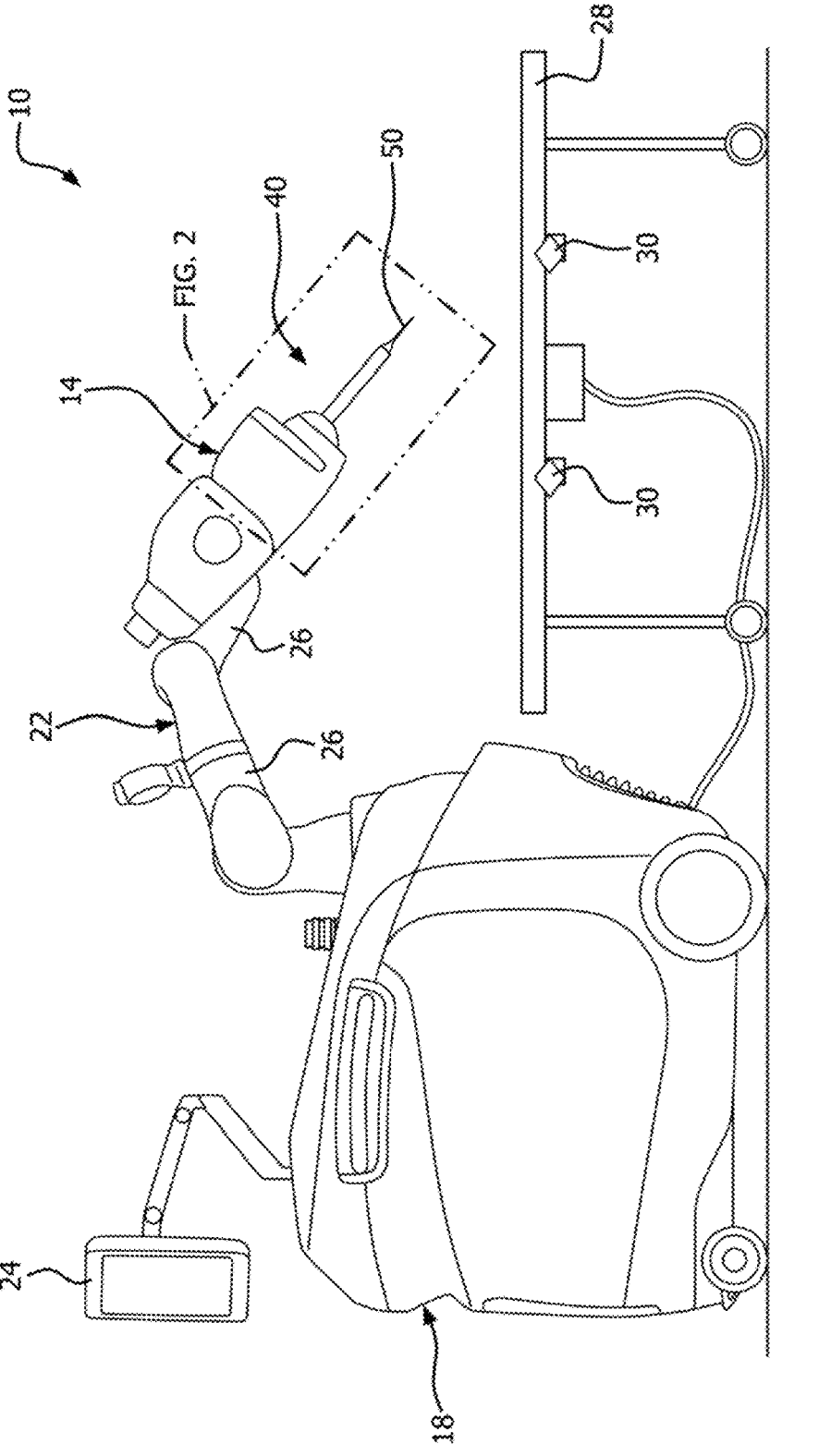
FIG. 1 is a side elevation of an intensity and dose modulated radiosurgical needle system.
Figure 2:
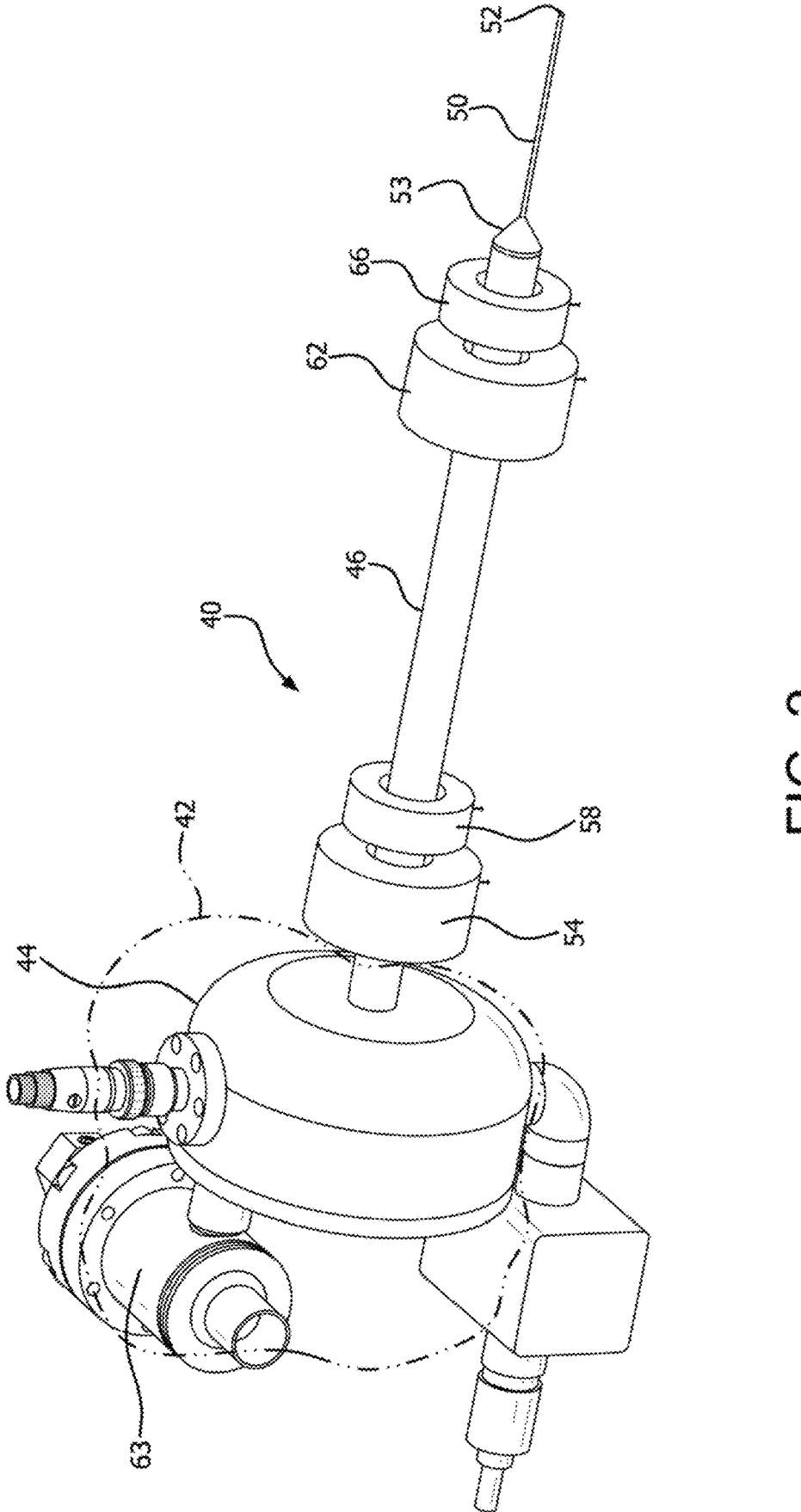
FIG. 2 is an enlarged perspective view, partially broken away, of area FIG. 2 in FIG. 1 showing a radiosurgical needle treatment head assembly for a radiosurgical needle system.
Figure 3:
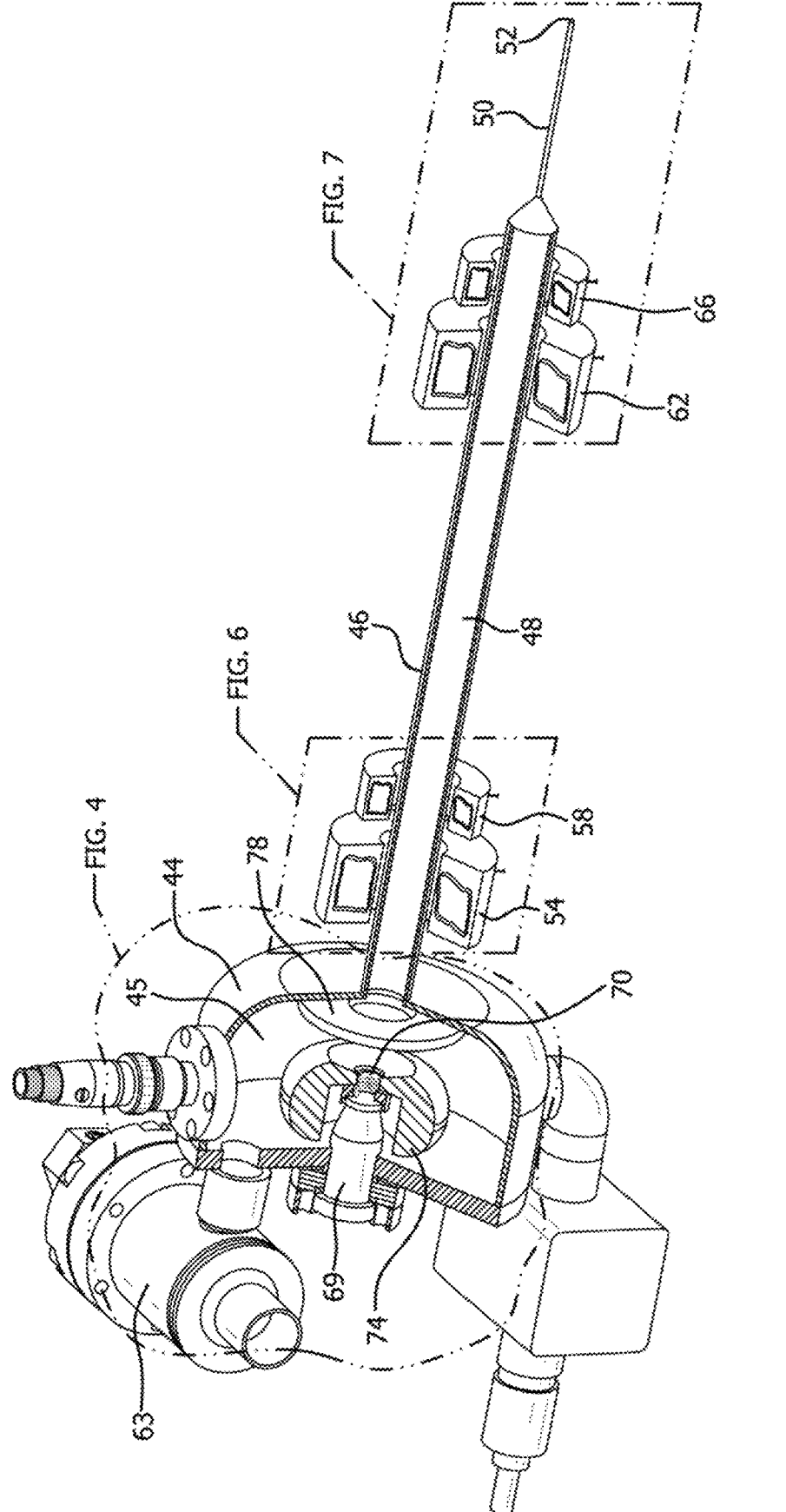
FIG. 3 is a perspective view, partially broken away, of the radiosurgical needle treatment head assembly of FIG. 2.
Figure 4:
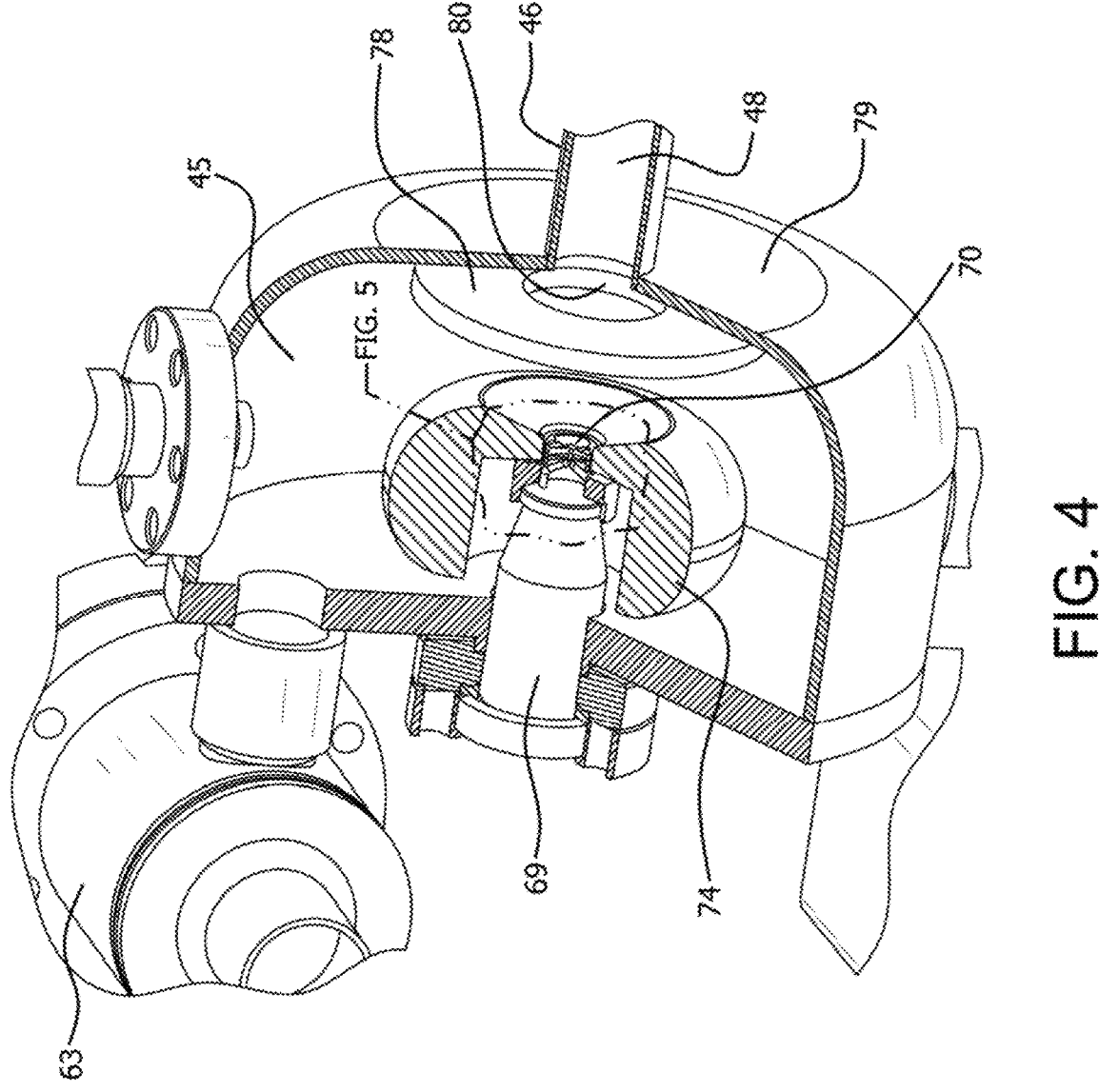
FIG. 4 is an expanded view of area FIG. 4 in FIG. 3.
Figure 5:
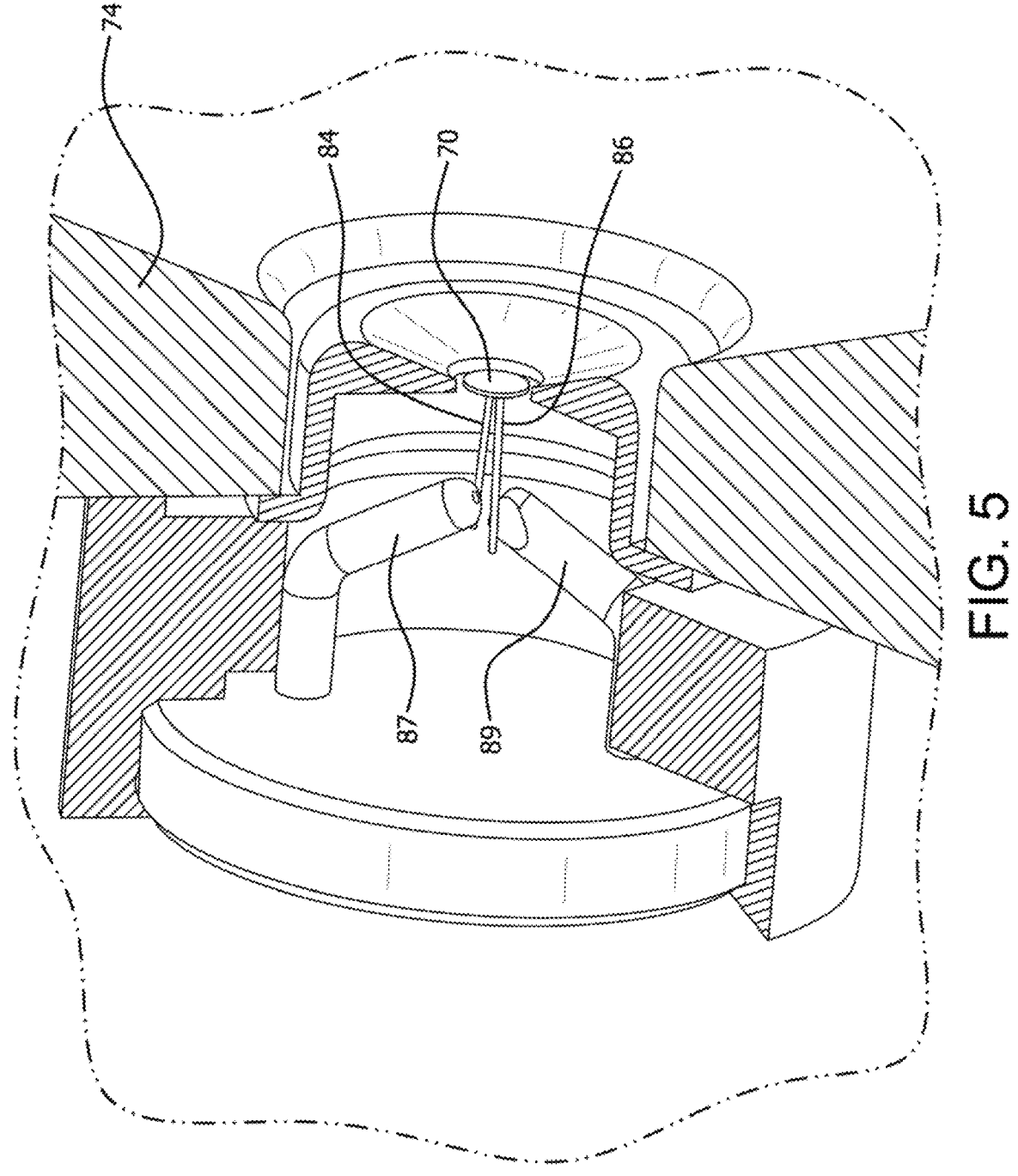
FIG. 5 is an expanded view of area FIG. 5 in FIG. 4.

A radiotherapy device according to the invention includes an electron source for generating an initial electron beam. A first beam corrector focuses the initial electron beam into a more concentrated and unidirectional focused electron beam. A target comprises a target material that when impacted by the focused electron beam generates Bremsstrahlung x-ray photons. A radiosurgical needle has an elongated radiopaque needle body portion having an interior lumen, a proximal end and a distal end. The radiosurgical needle further comprises a pointed tip at the distal end of the needle body portion for piercing the tissue of a patient. The target is positioned within the lumen of the radiosurgical needle and closer to the distal end than the proximal end. The distal end of the radiosurgical needle comprises a radiolucent portion for transmitting x-ray photons generated at the target. An elongated radiopaque micro drift tube has an open interior extending from the electron source to the radiosurgical needle. The micro drift tube has a proximal end nearest the electron source, and a distal end nearest the radiosurgical needle. The proximal end of the radiosurgical needle is affixed to the distal end of the micro drift tube. The open interior of the micro drift tube communicates with the lumen of the radiosurgical needle so as to define an electron flow path from the electron source to the target. A first beam steering device is provided for steering the focused electron beam within the micro drift tube to the target.

The radiotherapy device can further include a vacuum connection for connecting to a vacuum source for maintaining a vacuum within the open interior of the micro drift tube and the lumen of the radiosurgical needle.

The dimensions of the open interior of the micro drift tube, the lumen of the radiosurgical needle and the outside diameter of the radiosurgical needle can vary. The open interior of the micro drift tube can have a lateral cross-sectional diameter of from 1 to 5 mm. The open interior can have a lateral cross-sectional diameter of 1, 1.25, 1.5, 1.75, 2, 2.25, 2.5, 2.75, 3, 3.25, 3.5, 3.75, 4, 4.25, 4.5, 4.75, or 5 mm. The lateral cross-sectional diameter of the open interior of the micro drift tube can have a range of any high value and low value selected from these values. The open interior can have larger or smaller values depending on the intended use.

The lumen of the radiosurgical needle can have a diameter of from 1 to 5 mm. The lumen of the radiosurgical needle can have a lateral cross-sectional diameter of 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9 or 5 mm. The lateral cross-sectional diameter of the lumen of the radiosurgical needle can have a range of any high value and low value selected from these values. The diameter of the lumen can also have larger or smaller values than these values depending on the intended use.

The outside diameter of the needle body portion of the radiosurgical needle can be from 1 to 5 mm. The outside diameter of the needle body portion of the radiosurgical needle can be 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9 or 5 mm. The outside diameter of the needle body portion of the radiosurgical needle can have a range of any high value and low value selected from these values. The outside diameter can have larger or smaller values than these values, depending on the intended use.

The pointed tip of the needle can have varying dimensions relative to the outside diameter of the needle body portion. The diameter of the pointed tip can be, for example, 10, 25, 50, 75, 100, 150, 200, 250, 300, 350, 400, 450, 500, 550, 600, 650, 700, 750, 800, 850, 900, 950, 1,000, 1,050, 1,100, 1,150, 1,200, 1,250, 1300, 1,350, 1,400, 1,450, 1,500, 1,550, 1,600, 1,650, 1,700, 1,750, 1,800, 1,850, 1,900, 1,950, 2,000, 2,050, 2,100, 2,150, 2,200, 2,250, 2,300, 2,350, 2,400, 2,450, 2,500, 2,550, 2,600, 2,650, 2,700, 2,750, 2,800, 2,850, 2,900, 2,950, 3,050, 3,100, 3,150, 3,200, 3,250, 3,300, or 3,350 microns. The pointed tip can have a diameter within a range of any high value or low value selected from these values.

The surface area of the target that is reachable by the beam is within the lumen and can be quite small. The surface area of the target that is reachable by the electron beam can be from 0.5 to 20 mm². The surface area of the target that is reachable by the electron beam can be 0.5, 0.75, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5 or 20 mm², and can have a range of any high value and low value selected from these values.

The pointed tip can include an open space defined by interior tip walls. The target material can be affixed to the interior tip walls. The open space of the pointed tip communicates with the lumen of the radiosurgical needle to permit the focused electron beam to travel through the lumen and the open space of the pointed tip and strike the target material affixed to the interior tip walls.

The target material can be at the pointed tip, and alternatively can also be provided proximal to the pointed tip. The target material can span the lumen of the radiosurgical needle or only some cross-sectional portion of the lumen.

The radiolucent portion of the radiosurgical needle can be provided at varying positions in the radiosurgical needle. The purpose of the radiolucent portion is to permit x-ray photons generated at the target to be transmitted from the radiosurgical needle to the tumor or other patient body part that is being treated. The position of the radiolucent portion will determine the location of the emanation of the generated x-ray photons, and accordingly the area of treatment relative to the position of the radiosurgical needle. The radiolucent portion of the radiosurgical needle can be provided in the pointed tip, wherein x-ray photons generated at the target material will be transmitted through the pointed tip. This will emit more forwardly and sideways directed x-ray photons relative to the axis of the radiosurgical needle and the position of the pointed tip. The radiolucent portion of the radiosurgical needle can be provided proximal to the target material so as to transmit x-ray photons proximal to the target material. The target will emit x-ray photons in a more rearwardly and sideways direction relative to the axis of the radiosurgical needle and the needle tip.

The target material can be any suitable material which when struck by an electron beam will generate x-ray photons. The target material can include at least one selected from the group consisting of molybdenum, tungsten and gold. Combinations of these materials, combinations with other materials, or entirely other target materials are possible.

The target material can be disposed on a substrate. The substrate can be at least one selected from the group consisting of beryllium, aluminum, sapphire, diamond, alumina, and boron nitride. It is also possible that the target material would not need a substrate, or that the material forming the radiosurgical needle is radiolucent, and thus the radiolucent portion could be eliminated, for example in the case of a pointed tip made of the target material. The Bremsstrahlung x-ray photons generated at the pointed tip formed by the target material would be emitted directly to the patient body and without passage through a radiolucent portion of the radiosurgical needle.

The radiolucent portion can be made of varying materials. In addition to being radiolucent, the material can be compatible with insertion into the patient's body, capable of being sterilized, and impenetrable to air or body liquids. One such radiolucent material includes silicon carbide. Other possible radiolucent materials are possible.

It is possible to coat the radiosurgical needle with a coating to provide further sterility. A variety of coating materials are possible, including polymers, ceramics, and nano materials.

The radiotherapy device can include a robotic guidance system for moving the radiosurgical needle to a treatment location within a patient, and for withdrawing the radiosurgical needle from the treatment location. The electron source, beam corrector, beam steering device, drift tube, and radiosurgical needle can be provided in a treatment head. The treatment head can be connected to the robotic support. The robotic guidance system can comprise a robotic arm capable of three-dimensional movement.

The radiotherapy device can include a processor for receiving treatment planning data and patient position data. The processor processes the treatment planning data and the patient position data to move the robotic guidance system and the radiosurgical needle to a treatment location within the patient and to cause the electron source, the beam corrector and the beam steering device to direct the beam to a target with a beam energy and for a duration according to the treatment plan.

The radiotherapy treatment device can include or can be used with image guidance assisting devices which assist in guiding the radiosurgical needle to the proper position within the patient. Examples of suitable image guidance devices include x-ray tomography, ultrasound and photoacoustics. The image guidance devices communicate with the processor to assist in positioning the radiosurgical needle and adjusting the treatment plan which can affect parameters such as the steering of the beam by the beam steering device, the beam energy from the electron source, and the dose and pulse duration.

Guidance assisting devices can be affixed to a position on the body of the patient. The position of the guidance assisting device can then be sensed and reported to a processor, which uses the location information to place the radiosurgical needle relative to a desired position relative to the guidance device and thus the patient's body and the treatment area therewithin. One such guidance device is a guidance device or plate with holes dimensioned to receive the radiosurgical needle.

The radiotherapy device can include a second beam corrector. The second beam corrector is distal to the first beam corrector and the first beam steering device, and closer to the proximal end of the radiosurgical needle than the first beam corrector. The second, distal beam corrector acts on the focused electron beam to produce a refocused electron beam at a distal end of the micro drift tube. Any number of beam correctors are possible. The locations of such beam correctors can be varied.

The radiotherapy device can also include a second, distal beam steering device. The second beam steering device is distal to the first beam corrector and the first beam steering device, and closer to the proximal end of the radiosurgical needle than the first steering device. The second beam steering device steers the refocused electron beam to the target. Any number of beam steering devices are possible. The locations of such beam steering devices can be varied.

A method for conducting radiotherapy can include the steps of providing a radiosurgical needle with an elongated radiopaque needle body portion having an interior lumen, a proximal end and a distal end. The distal end comprises a pointed tip for piercing the tissue of a patient. The radiosurgical need further comprises a target comprising target material that when impacted by the focused electron beam generates Bremsstrahlung x-ray photons. The target is positioned within the lumen and closer to the distal end than the proximal end. The distal end of the radiosurgical needle can include a radiolucent portion for transmitting x-ray photons generated at the target.

The radiosurgical needle is inserted into the body of a patient by piercing a tissue of the patient with the pointed tip and advancing the radiosurgical needle to a patient therapy location, for example the location of a tumor. A focused and steered electron beam is directed at the target, wherein Bremsstrahlung x-ray photons will be generated at the target and will be transmitted through the radiolucent portion to the patient therapy location.

There is shown in FIGS. 1-7 a radiotherapy system 10 including a head unit 14 mounted to a base unit 18 by suitable structure such as a robotic arm 22. A processor 24 can be provided on the base unit 18 and can be a standalone processing system or connected by a communications link to a remote processor and database. A treatment head assembly 40 including a radiosurgical needle 50 is mounted to the treatment unit 14 for generating and administering therapeutic x-ray photons.

The robotic arm 22 can include a plurality of robotic arm articulation members 26 and actuators to facilitate movement with respect to each of the articulation members 26. More articulation members 26 will provide more freedom of movement of the head unit 14. The robotic arm can include a plurality of joint position sensors which can provide position information to the processor 24 to determine oppose of the robotic arm. This information can be used for determining an exact location and orientation of the treatment head 40 relative to the patient undergoing therapeutic radiation treatment. The patient can be positioned on a treatment support 28 which can include one or more position sensors 30 which communicate the position of the patient on the patient support 28 to the processor 24.

The robotic arm can in some instances provide freedom of movement about multiple orthogonal axes and include lightweight force and torque sensors to ensure safe operation with humans without the need for a safety fence. Exemplary robots of this kind are commercially available from various sources. For example, KUKA AG of Augsburg Germany manufactures a line of direct human robot collaboration (HRC) capable lightweight robots which are suitable for direct human-robot interaction. Robots of this kind are well-suited for the delicate operations described herein because they include high-grade joint torque sensors included all six axes, which can detect the slightest of external forces resulting from contact with objects, can respond by immediately reducing the level of force and speed associated with robot movements. The robotic arm 18 will precisely maintain the position of the x-ray treatment head 40 relative to a subject patient. In order to accomplish this result, the robotic arm can move along multiple motion axes, up to seven motion axes, to maintain a relative position of the radio surgical needle at a particular location and/or along a predetermined movement path.

The treatment head 40 is comprised of an electron beam generator (EBG) 42, a micro drift tube 46 and a radiosurgical needle 50 having a pointed tip 52. The drift tube 46 is connected to the radiosurgical needle 50 by suitable structure such as neck portion 53. A first beam corrector 54 and a first beam steering device 58 are provided. More beam focusing units and being steering devices can be provided, for example, a second, distal beam focusing unit 62 and a second, distal beam steering device 66.

The treatment head 40 generates a steerable x-ray energy beam the diameter of which can be less than 30 mm and, in some scenarios, can be less than 10 mm although other dimensions are possible. The drift tube 46 has an open interior 48 which extends some distance from the electron beam generator 44. The length of the drift tube 46 can vary, for example from 10 cm to 50 cm, although other dimensions are possible.

Electron beam generators are well-known in the art and different designs are possible for the electron beam generator 42. The electron beam generator 42 can comprise an envelope 44 which encloses a vacuum chamber 45. A vacuum source connection 63 maintains a vacuum within the electron beam generator 42, the drift tube 46, and the lumen 51 of the radiosurgical needle 50. Within the vacuum chamber is a high voltage connector 69 for providing high negative voltage to a cathode 70. A suitable high voltage applied to the cathode for purposes of x-ray generation would be in the range of –50 kV and –250 kV. Also enclosed in the vacuum chamber is a field shaper 74 and a repeller 78 having an interior opening 80 for the passage of electrons to the drift tube 46. The cathode 70, when needed, serves as a source of electrons, which are accelerated by the high voltage potential between the cathode 70 and the anode. In the present embodiment, the anode is the envelope 44, and the repeller 78, where the envelope 44 is at ground voltage and the repeller 78 is at a small positive voltage with respect to ground.

The function of the repeller 78 is to repel any positively charged ions that might be generated in the drift tube 46, thus preventing those ions from entering the region of the cathode 70 where they might cause damage. The function of the field shaper 74 is to provide smooth surfaces which control the shape and magnitude of the electric field caused by the high voltage. The grid 79 provides a desired shape to the electric field in the vicinity of the cathode 70, as well as allowing the admission of electrons from the cathode 70 to be shut off. The cathode 70 is fixed to the legs of the heater 84, 86, which are typically made from a metallic material that has both high electrical resistivity resistance to thermal degradation, thus allowing an electric current flowing through the heater legs to generate a high temperature that heats the cathode 70. The electrical connections to the heater legs 84, 86 are provided by connector pins 87, 89, which connect the heater legs 84, 86 to the high-voltage connector 69.

The drift tube 46 can comprise a material such as stainless steel or silicon carbide. Alternatively, the drift tube 46 can be comprised of the ceramic material such as aluminum or aluminum nitride. If the drift tube structure is not formed of a conductive material, then it can be provided with a conductive interlining. The interlining can be comprised of copper, titanium alloy or other material which can be applied by suitable processes such as sputtering, evaporation, and other means to the interior surface of the drifting. The hollow interior 48 of the drift tube is open to the vacuum chamber 45, such that the interior 48 of the drift tube 46 is also maintained at a vacuum pressure. A suitable vacuum pressure for purposes of the invention can be in the range of about $10^{-5}$ torr to about $10^{-9}$ torr. Other vacuum pressures are possible.

The interior 48 of the drift tube 46 is maintained at a vacuum and the drift tube 46 is maintained at ground potential. Accordingly, the momentum imparted by the electrons will continue to ballistically carry the electrons down the length of the drift tube 46 at a very high velocity approaching the speed of light toward the radiosurgical needle 50, where the electrons will travel through the lumen 51 of the radiosurgical needle 50 to the target.

The beam corrector 54 is provided to confine a beam vortex of electrons traveling along the length of the drift tube 46. For example, such convergence operations can involve adjusting the beam to a concentrated beam of electrons traveling to the target of the radiosurgical needle 50. As such, the beam corrector 54 can be comprised of a plurality of magnetic coils which are controlled by selectively varying applied currents therein. The applied electric currents cause each of the plurality of magnetic focusing coils to generate a magnetic field. The magnetic fields penetrate into the drift tube 46 substantially in the region enclosed by the beam corrector 54. The presence of the penetrating magnetic fields causes the electron beam to correct into an aligned concentrated beam sometimes known as a pencil beam.

The beam steering device 58 is comprised of a plurality of selectively controllable magnetic steering coils. Steering coils are arranged to selectively vary a direction of travel of electrons traveling within the drift tube 46. The magnetic steering coils achieve this result by generating a magnetic field when energized with an electric current. The magnetic field exerts a force selectively upon the electrons traveling within the drift tube 46, thus varying the electron beam direction of travel. As a result of such deflection of the electron beam direction of travel, a location where the beam strikes a target element of the radiosurgical needle 50 can be selectively controlled.

Figure 6:
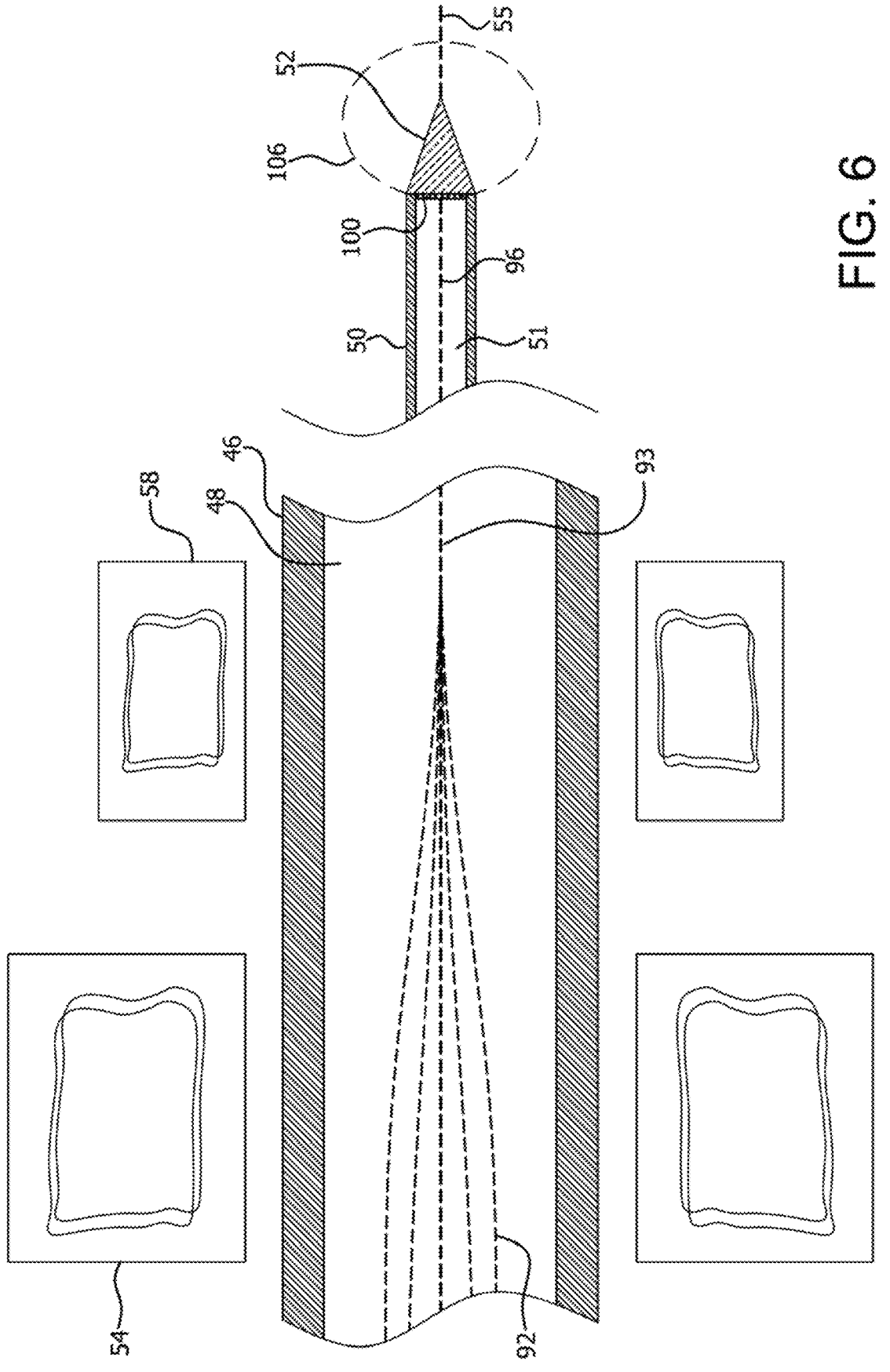
FIG. 6 is an expanded cross section, partially broken away, of area FIG. 6 in FIG. 3.

There is shown in FIG. 6 a schematic depiction of the operation of the beam corrector 54 and the beam steering device 58. The electron vortex 92 leaving the electron beam generator 42 is acted upon by the magnetic field generated by the beam corrector 54 and focused into a more concentrated, unidirectional and focused beam 93. The focused beam 93 can then be acted upon by the beam steering device 58. Beam steering device 58 generates a magnetic field which to vary the direction of travel of the focused beam 93. In the example shown in FIG. 6, the focused and steered electron beam 96 is aligned with the longitudinal axis 55 of the lumen 51 of the radiosurgical needle 50. The focused and steered electron beam 96 is directed at a target 100 within the lumen 51 such that x-ray beam 106 is generated in a controlled and consistent manner according to the treatment plan.

Figure 7:
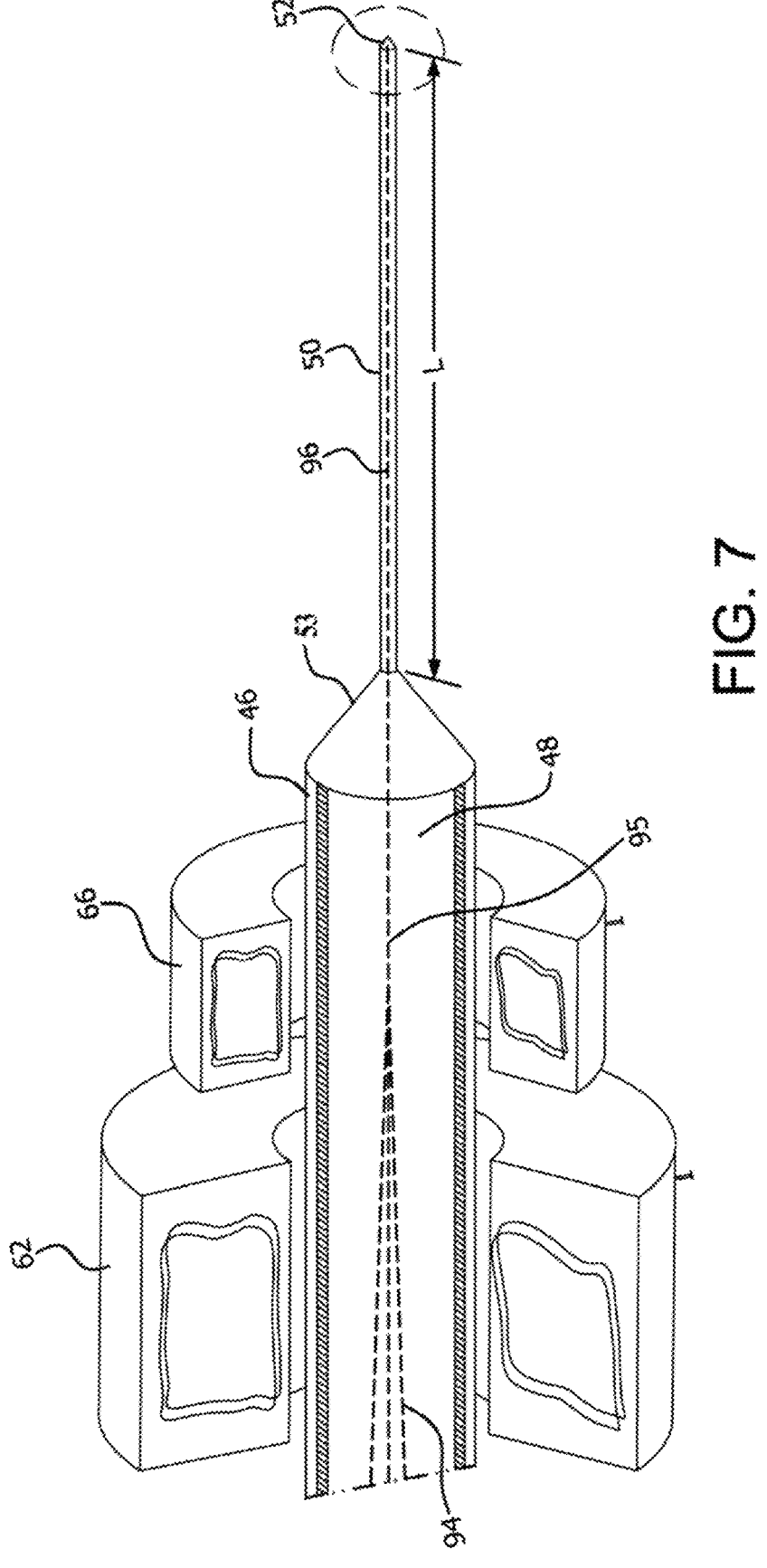
FIG. 7 is an expanded perspective view, partially broken away, of area FIG. 7 in FIG. 3.

There is shown in FIG. 7 an embodiment in which a second, distal beam corrector 62 and a second, distal beam steering device 66 are provided. The focused and steered electron beam 93 shown in FIG. 6 can over the length of the drift tube 46 become somewhat dispersed and can become somewhat misaligned as shown by dispersed electron beam 94. The second beam corrector 62 generates a magnetic field which re-compresses the electron beam 94 into a reconcentrated and unidirectional electron beam 95. The second beam steering device 66 generates a magnetic field which redirects the electron beam 95 to a redirected electron beam 96 aimed at the desired location on the target 100.

Figure 8:
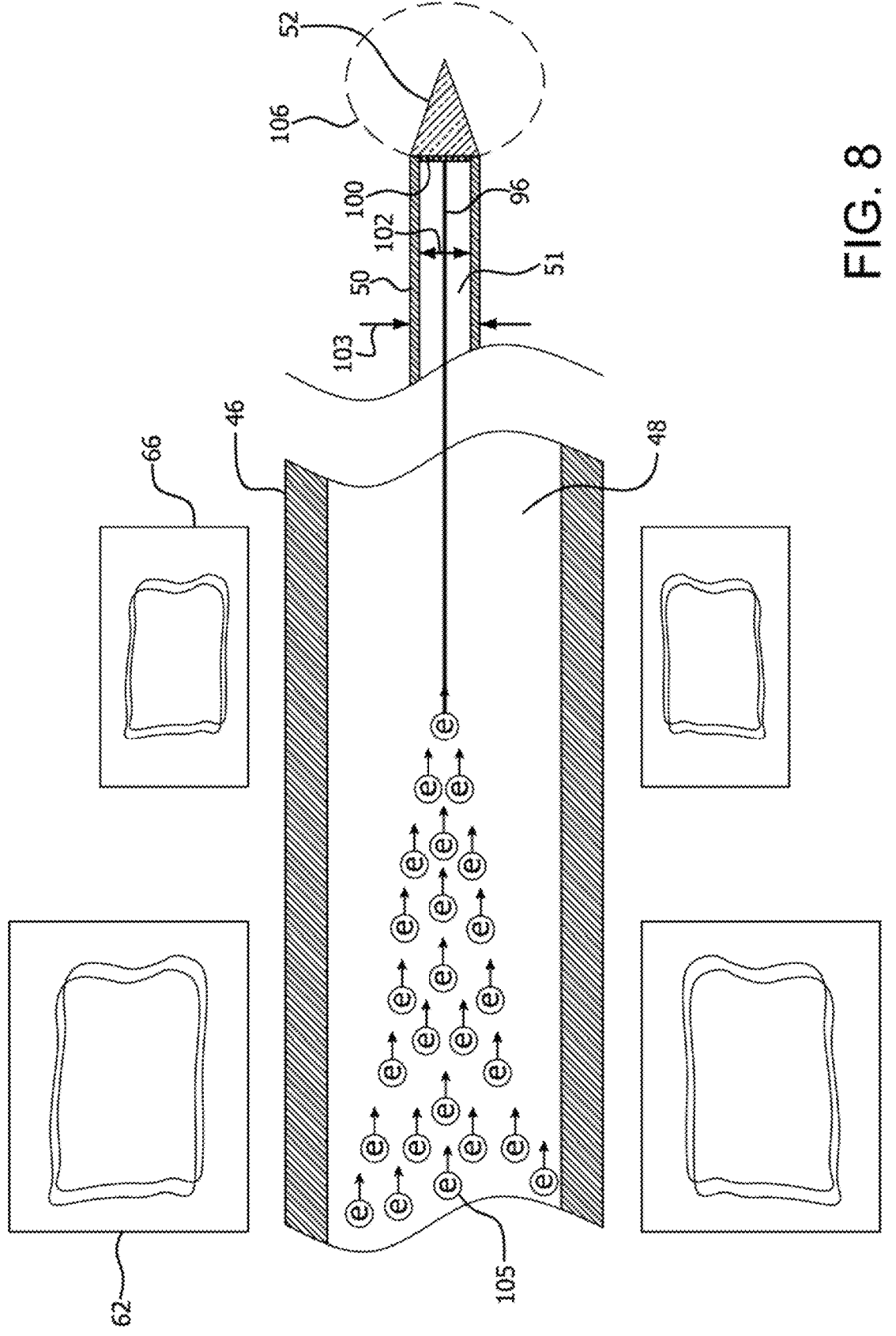
FIG. 8 is a schematic cross section illustrating the operation of distal focusing and steering coils, in a first mode of operation.
Figure 9:
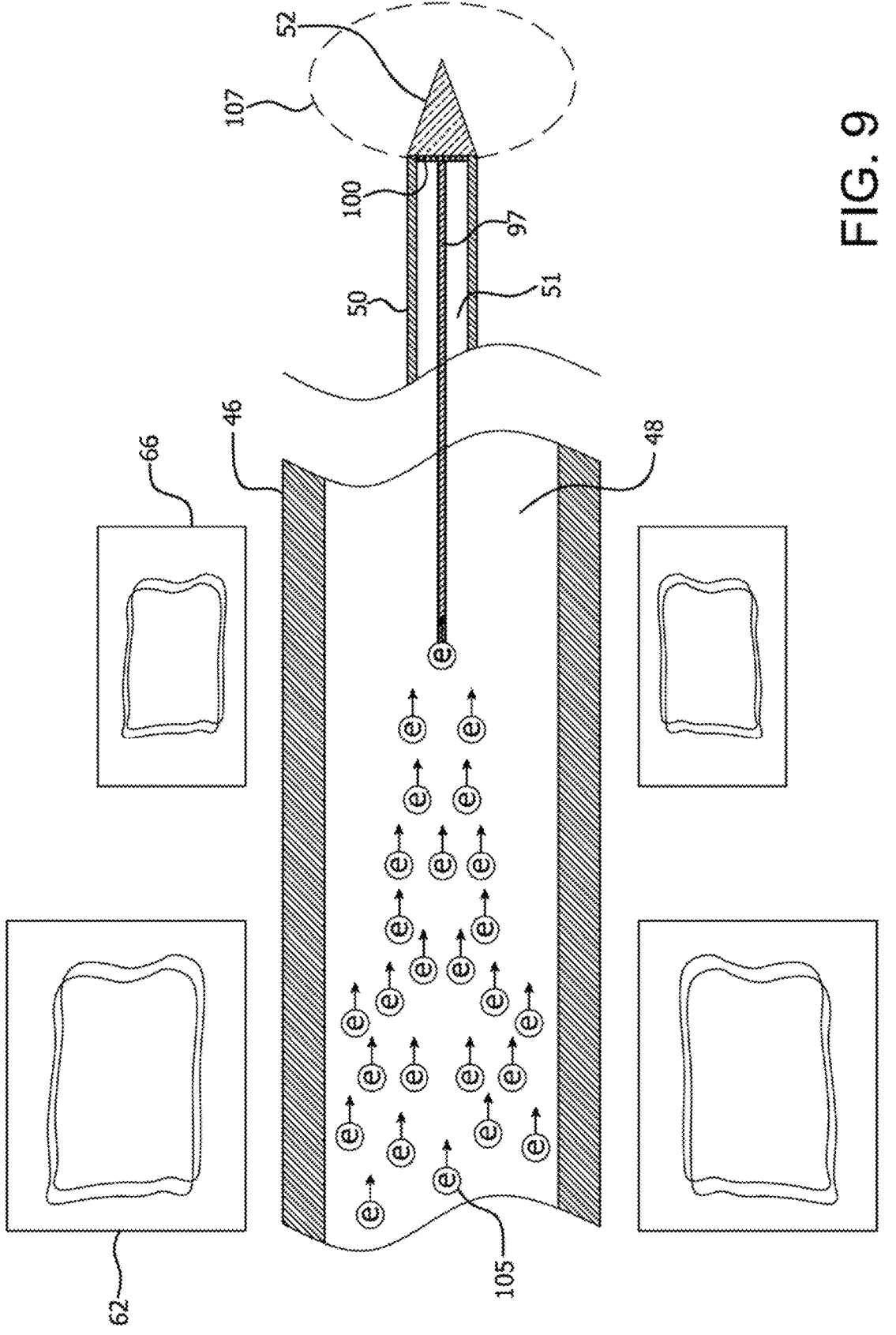
FIG. 9 is a schematic cross section illustrating the operation of the distal focusing and steering coils, in a second mode of operation.
Figure 10:
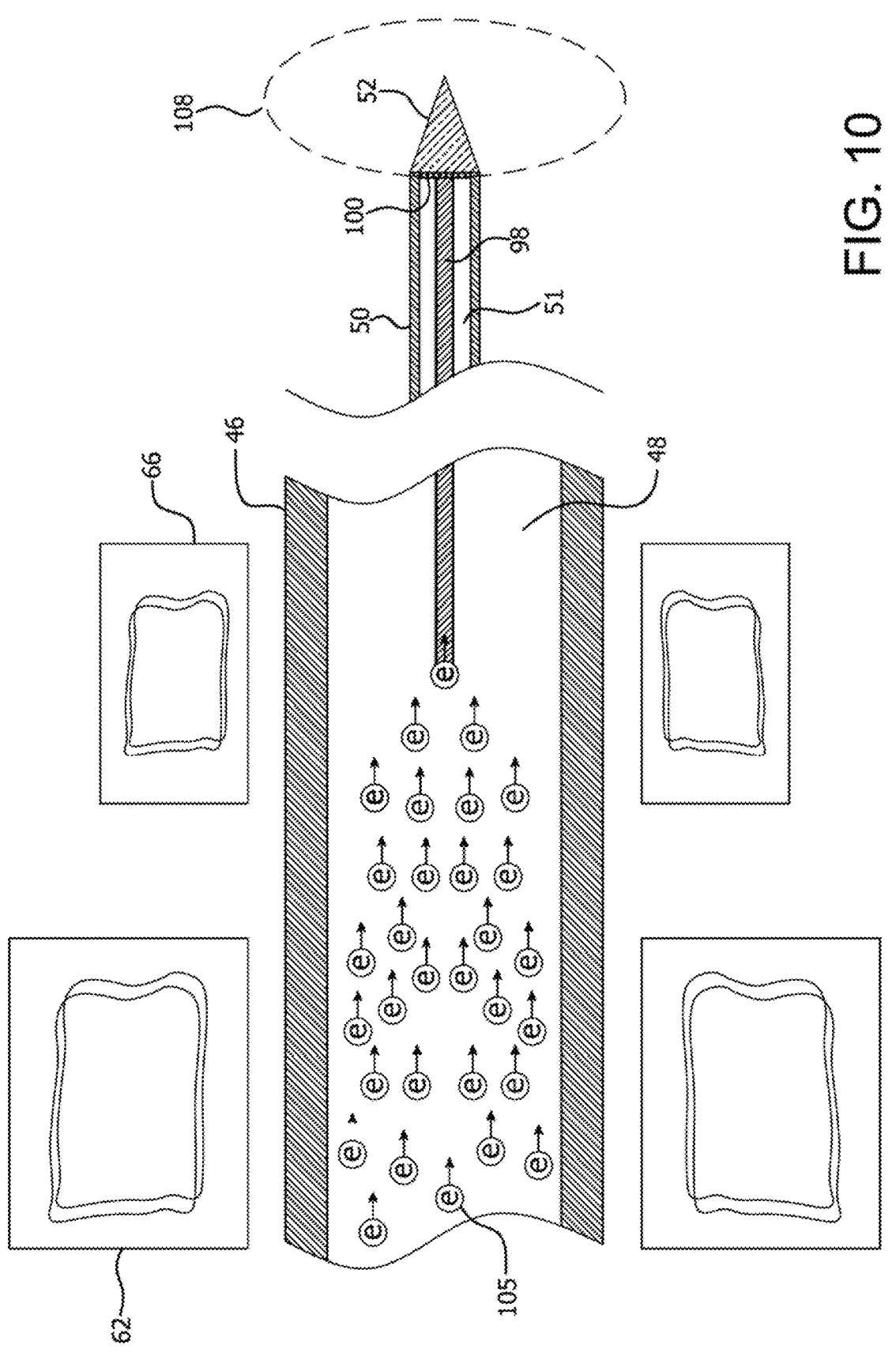
FIG. 10 is a schematic cross section illustrating the operation of the distal focusing and steering coils, in a third mode of operation.

There is shown in FIGS. 8-10 the operation of the beam correctors and beam steering devices of the invention. As shown in FIG. 8, dispersed electrons 105 are acted upon by the distal beam corrector 62 and the distal beam steering device 66 to form a tightly concentrated and directed beam 96 which when striking the target 100 generates an x-ray beam field 106. The radiosurgical needle 50 has an outside diameter 103 and the lumen 51 has a diameter 102 which are preferably only 5 mm or less, and accordingly, very precise control of the beam 96 is necessary. As shown in FIG. 9, the dispersed electrons 105 can be acted upon by the distal beam corrector 62 and distal beam steering device 66 to form a refocused and redirected beam 97 that is greater in diameter than the beam 96 and when striking the target 100 generates a larger x-ray beam field 107. This can be required by the parameters of the treatment plan, and by appropriate control of the magnetic fields of the beam correctors 54, 62 and the beam steering devices 58, 66 the desired beam can be so formed. There is shown in FIG. 10 an electron beam 98 which is still greater in diameter and when striking the target 100 produces a still more dispersed x-ray beam field 108 as may be required by the treatment plan.

Figure 11:
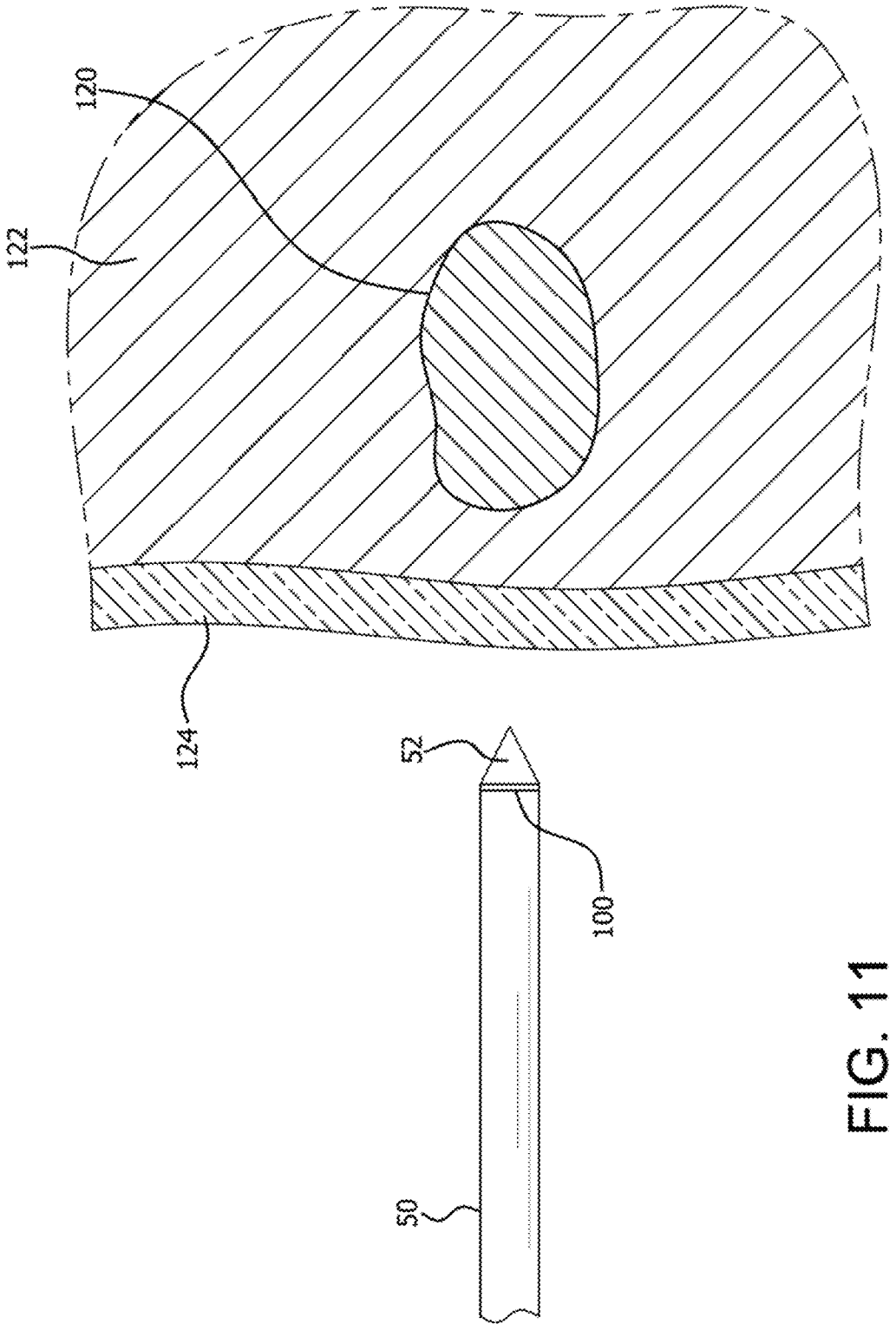
FIG. 11 is a schematic depiction, partially in cross section, of the treatment of a tumor using the radiosurgical needle, in a first mode of operation.
Figure 12:
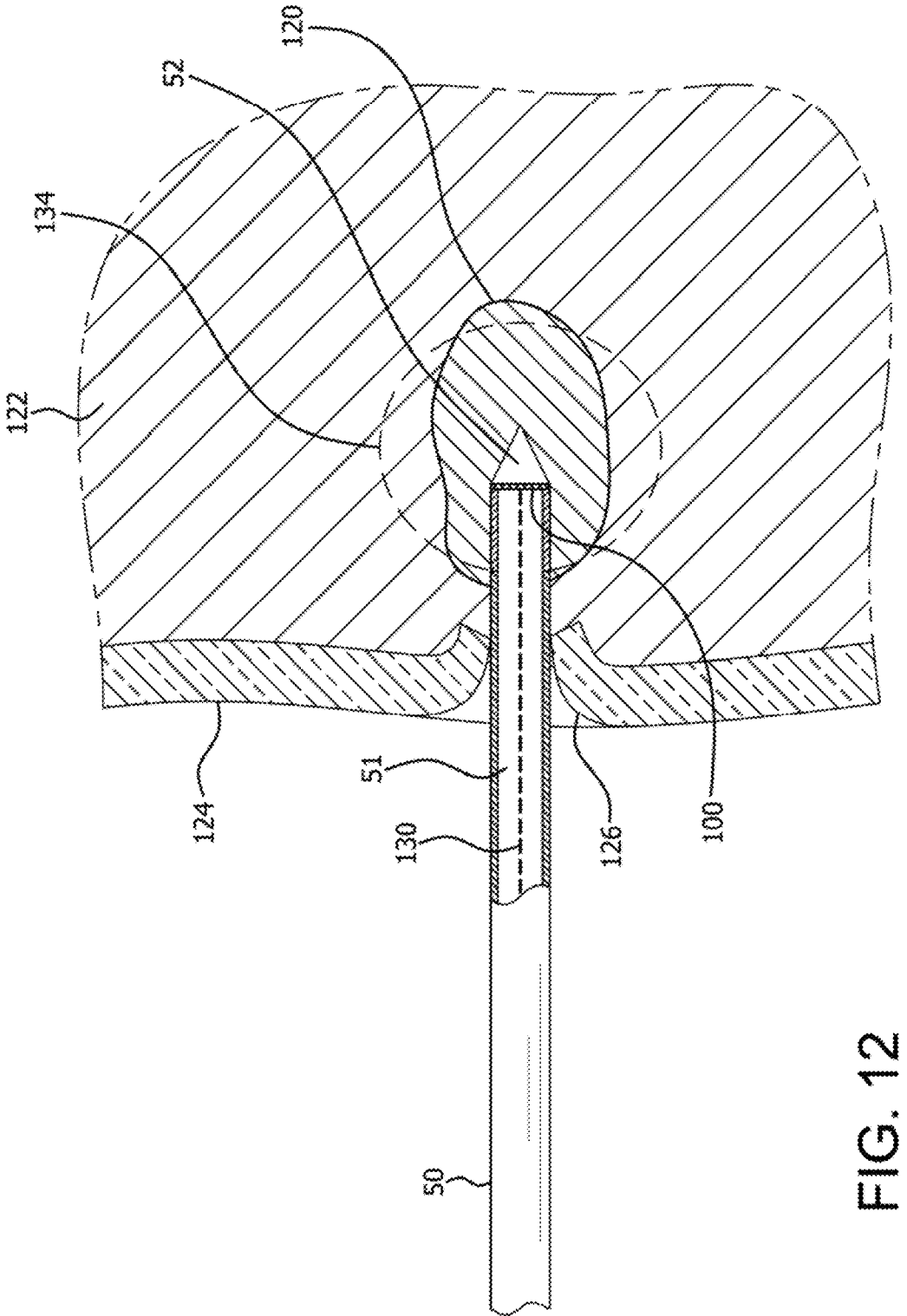
FIG. 12 is a schematic depiction, partially in cross section, of the treatment of a tumor using the radiosurgical needle, in a second mode of operation.
Figure 13:
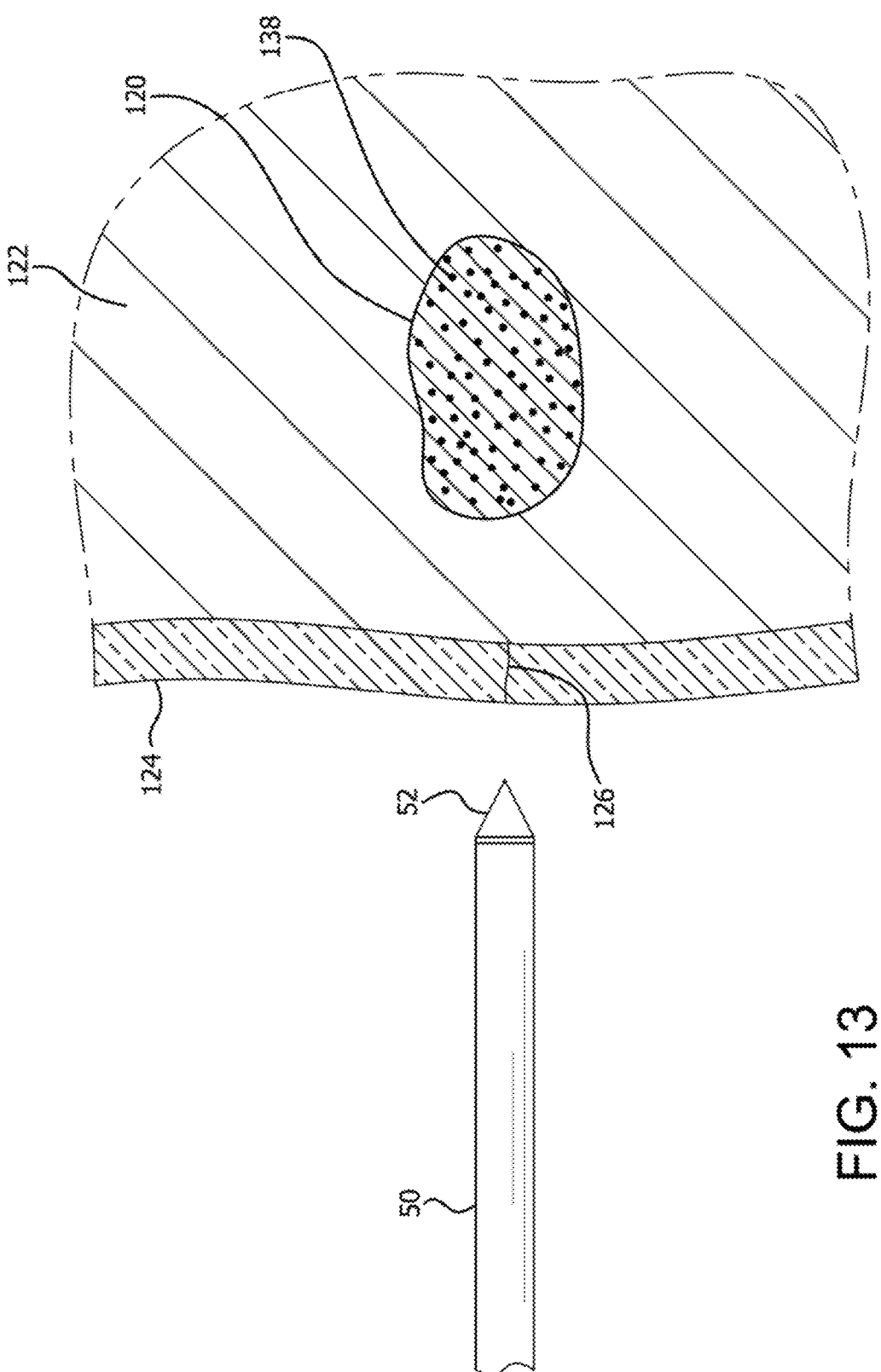
FIG. 13 is a schematic depiction, partially in cross section, of the treatment of a tumor using the radiosurgical needle, in a third mode of operation.

An example of the operation of the radiosurgical needle assembly of the invention is shown in FIGS. 11-13. The radiosurgical needle 50 bearing the pointed tip 52 and the target 100 is advanced toward the treatment area such as tumor 120. The movement of the radiosurgical needle 50 can be controlled by a robot such as the robotic arm 22 or other suitable robotic structures, which in turn are controlled by the processor according to the treatment plan and guidance information. The pointed tip 52 pierces the surface tissue 124 at a puncture location 126 and also pierces subsurface tissue 122 to reach the location of the tumor 120. The electron-beam generator 42 is then energized creating an electron beam 130 which travels through the lumen 51 of the radiosurgical needle 50 to strike the target 100. This generates an x-ray beam which passes through radiolucent portions of the radiosurgical needle 50. In the example of FIG. 12, the pointed tip 52 is radiolucent and thus the x-ray photons are emitted through the pointed tip 52 to create an x-ray beam field 134 which irradiates the tumor 120. The radiosurgical needle 50 can be further advanced or partially withdrawn to irradiate other portions of the tumor 120. The radiosurgical needle 50 is withdrawn (FIG. 13) and the puncture location 126 will reclose similarly to a hypodermic injection needle. Exposure to the x-rays leaves dead cells 138 in the tumor body 120 which can eliminate or partially eliminate the tumor 120. The radiosurgical needle 50 can be repositioned by the robot and reinserted into a different location in the patient to perform a treatment procedure in the different location, which can be within the same tumor body 120 or in a different tumor where there are multiple tumors within an organ such as the prostate. It is also possible to repeat the procedure within a period of time in the same location according to the treatment plan, where the guidance system and robot will return the radiosurgical needle 50 to the same position or a new position within the tumor 120 according to diagnostic imaging performed subsequent to the first treatment and a resulting revised treatment plan.

Figure 14:
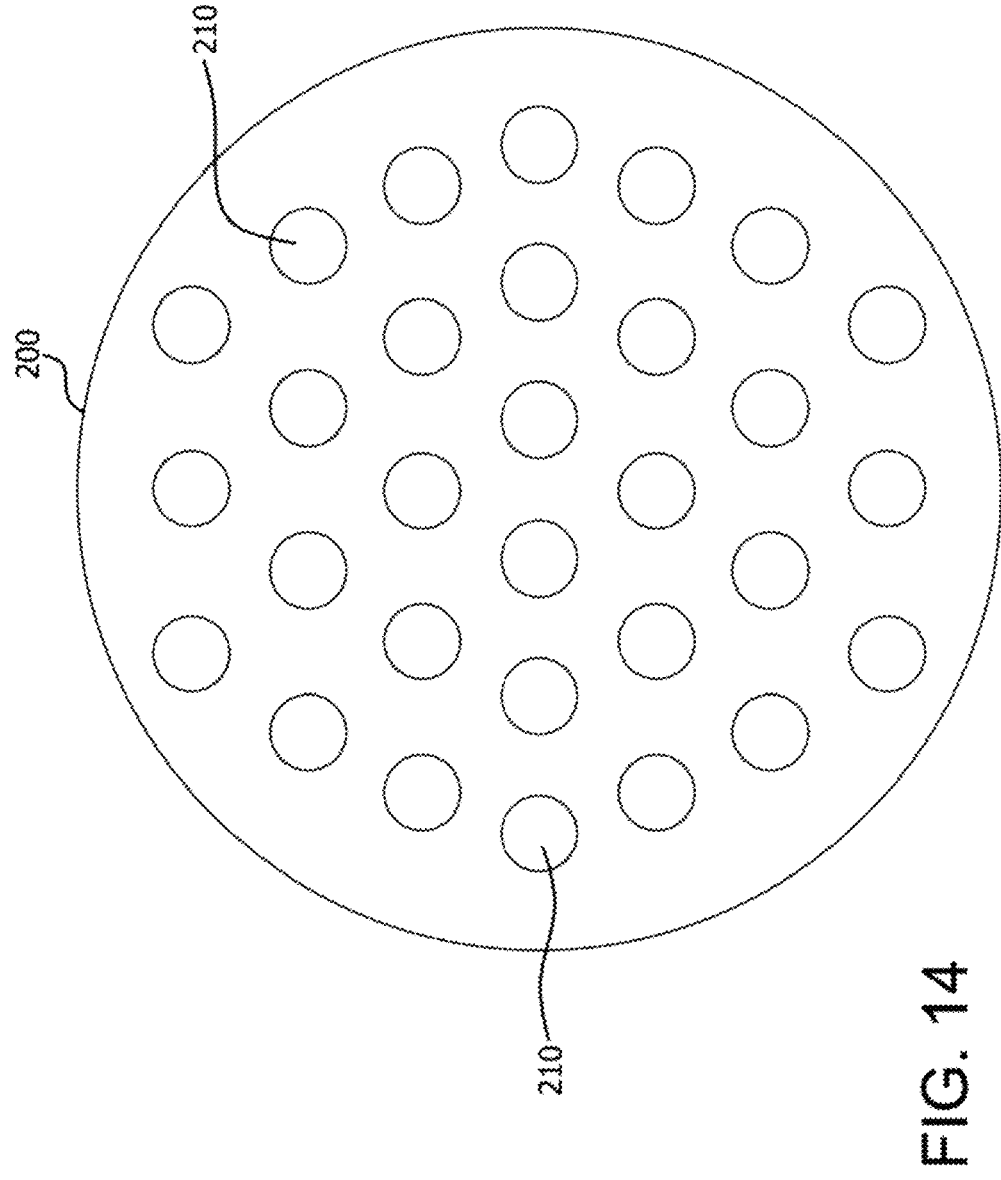
FIG. 14 is a plan view of a guidance template device for a radiosurgical needle system.
Figure 15:
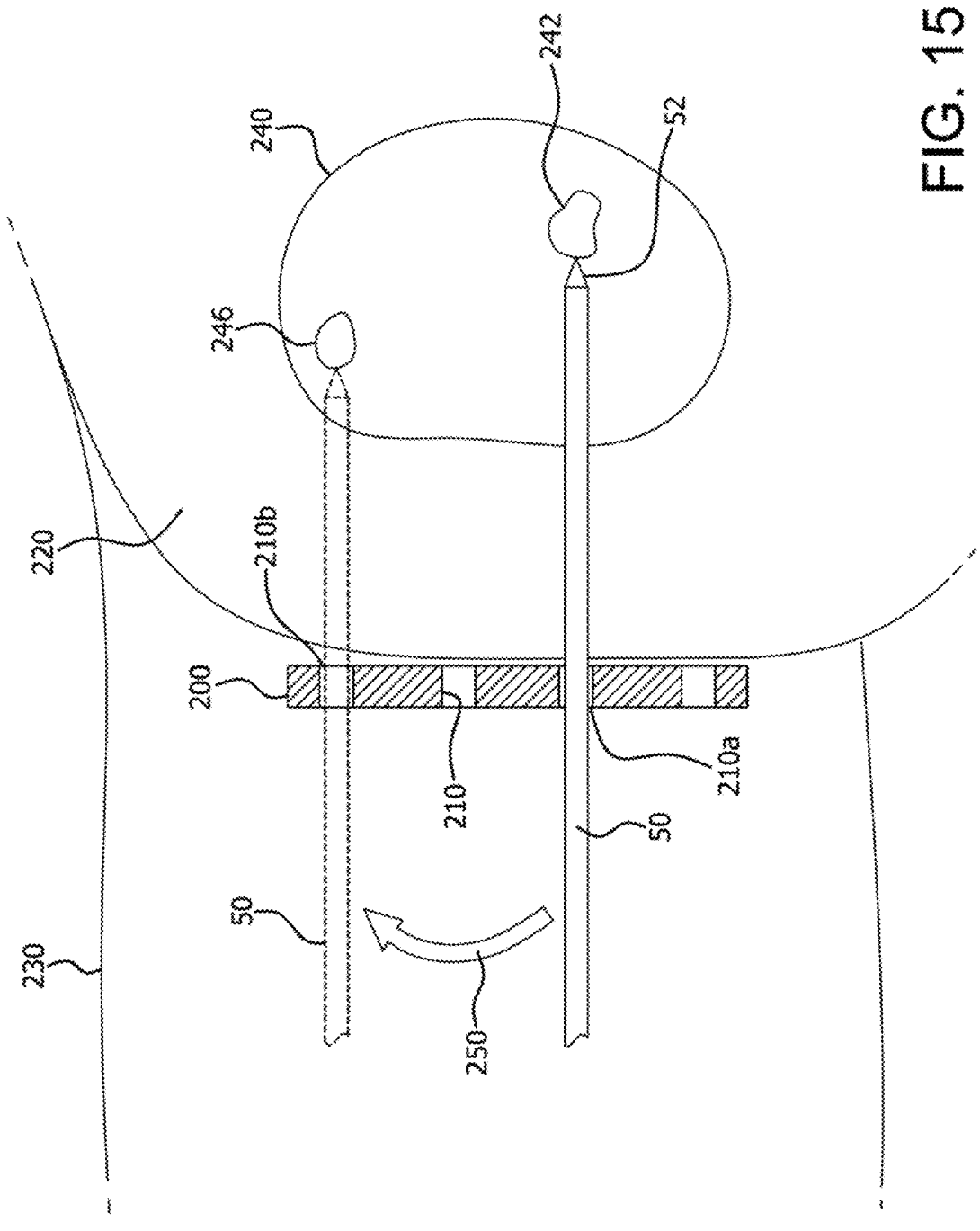
FIG. 15 is a schematic cross section illustrating the operation of the guidance device of FIG. 14.

Guidance for the positioning of the radiosurgical needle 50 can be accomplished by many different means. Surgical guidance systems are well-known in the art, and many such systems would be useful for the invention to position the radiosurgical needle 50 at a desired treatment location within the body and patient. Assistance to such guidance systems can be accomplished by the guidance device 200 shown in FIGS. 14-15. The guidance device 200 can be a planar body or template and can have a number of guidance apertures 210. The guidance device 200 is positioned on the body of the patient and serves as a point of reference for the guidance system. The radiosurgical needle 50 is advanced through selected ones of the apertures 210 according to the treatment plan. There is schematically shown in FIG. 15 the pelvic area 220 and leg 230 of the patient, and a prostate 240 with tumors 242 and 246. The radiosurgical needle 50 is advanced by the robot through a first aperture 210a to pierce the tissue of the patient and reach the location of the tumor 242 within the prostate 240. The electron-beam generator is energized and an x-ray beam field emitted to irradiate the tumor 242. The radiosurgical needle 50 is then withdrawn by the robot and repositioned as indicated by arrow 250. The radiosurgical needle 50 is then advanced by the robot through a different aperture 210b according to the treatment plan to reach the tumor 246, whereupon the electron beam generator is again energized to emit an x-ray photon beam field as required by the treatment plan.

Figure 16:
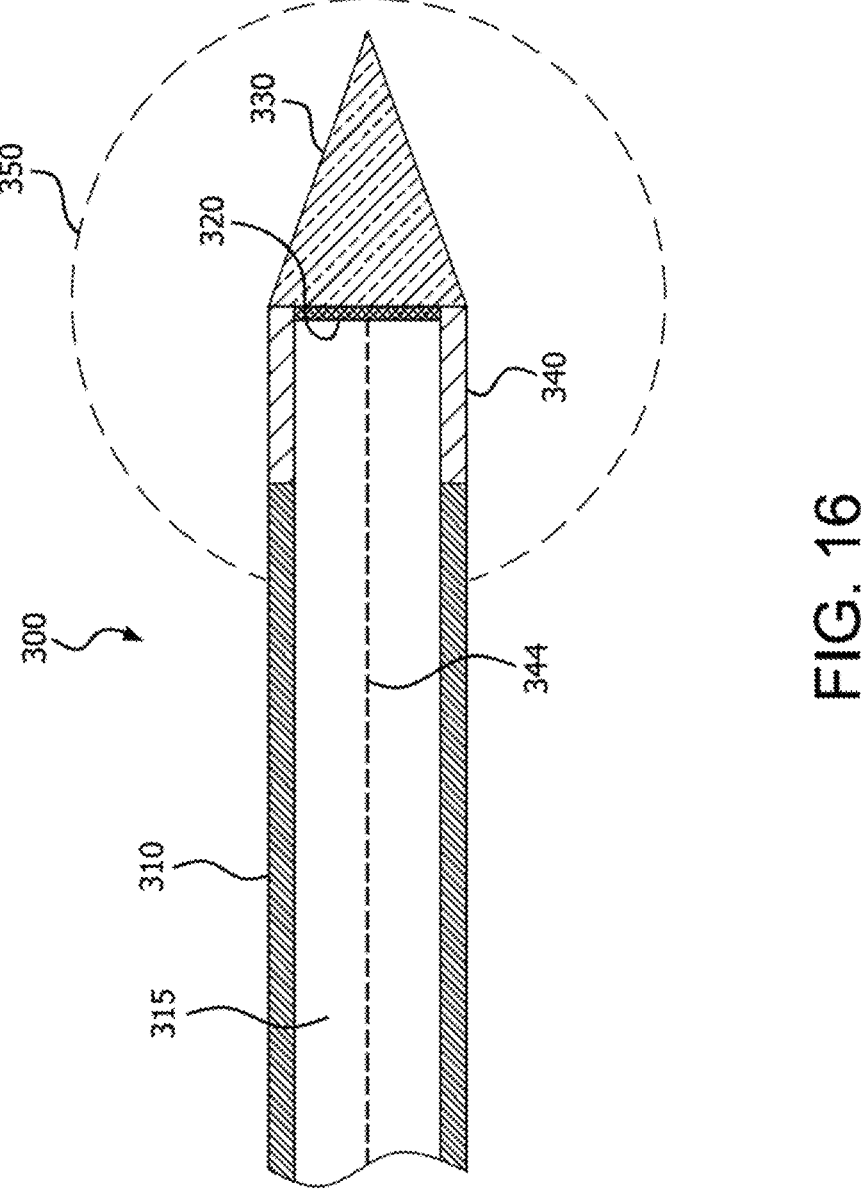
FIG. 16 is a schematic cross section of an alternative radiosurgical needle.

The position of the target and radiolucent portion of the radiosurgical needle 50 can be varied. Different radiosurgical needles 50 can be provided for different intended uses and according to different treatment plans. The location of the radiolucent portion will change the location, direction, size and shape of the x-ray photon treatment beam field. There shown in FIG. 16 an alternative radiosurgical needle 300 with a radiopaque needle body 310 defining an interior lumen 315 and a target 320 which spans a distal end of the lumen 315. A pointed tip 330 is distal to the target 320 and made of a rigid but radiolucent material. A radiolucent portion 340 is also provided as part of the distal end of the needle body proximal to the target 320. An electron-beam 344 is directed at the target 320 which will then emit x-ray photons. The pointed tip 330 and the proximal radiolucent portion 340 will emit an x-ray treatment beam field 350 that is both proximal and distal to the target 320. Other variations are possible.

Figure 17:
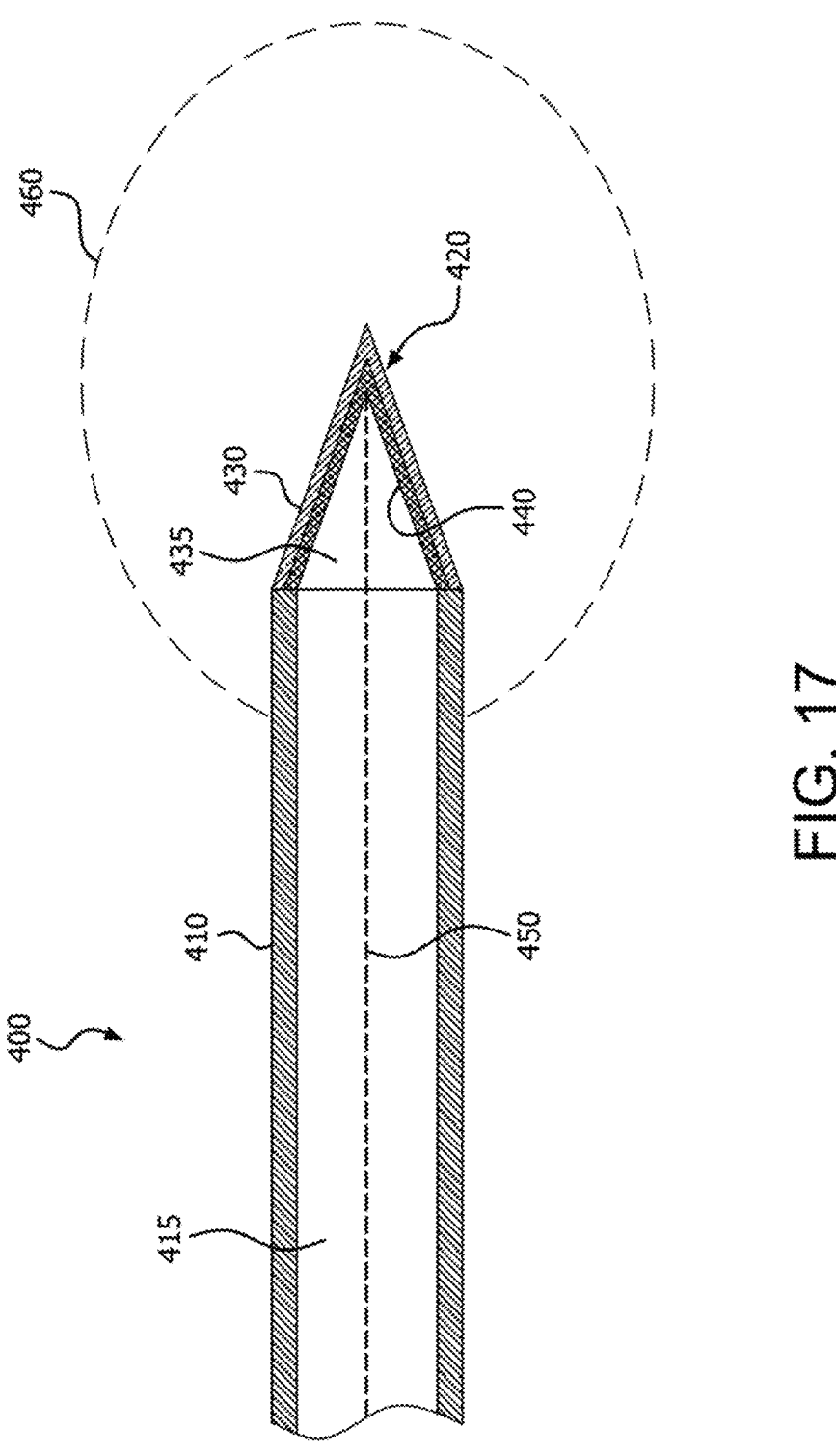
FIG. 17 is a schematic cross section of a second alternative radiosurgical needle.

There shown in FIG. 17 an alternative embodiment of a radiosurgical needle 400 with a needle body 410 defining an interior lumen 415. The radiosurgical needle 400 has a pointed tip 420 that is comprised of a conical substrate layer 430 made of a rigid and radiolucent material, and a target material 440 coating an interior surface of the substrate 430. The conical tip 420 defines an open conical interior space 435 which communicates with the lumen 415. The electron beam 450 generated by an electron-beam generator progresses through the lumen 415 and the interior space 435 to reach the target material 440. This generates x-ray photons at the target material 440 which are transmitted through the radiolucent substrate 430 to create a therapeutic x-ray beam field 460. The electron beam 450 can be steered or rastered to generate the therapeutic X-ray beam field in various locations of the target material 440.

Figure 18:
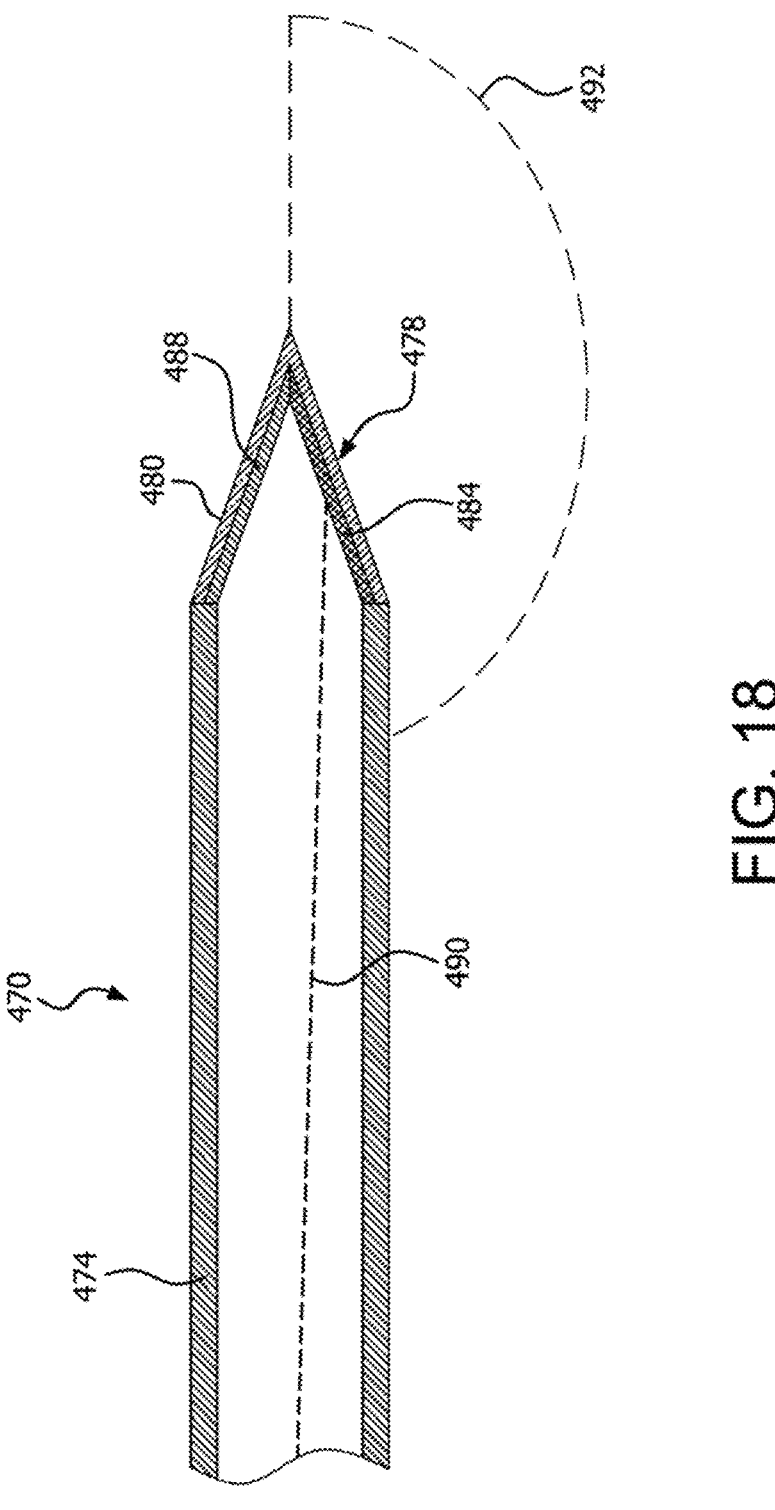
FIG. 18 is a schematic cross section of a third alternative radiosurgical needle.

There is shown in FIG. 18 an embodiment 470 of the radiosurgical needle having a needle body 474 and a tip 478. The tip 478 includes a substrate 480 which supports a target material 484 and a shielding material 488. The electron beam 490 is directed at the target material 484. In the embodiment shown in FIG. 18, the target material 484 covers approximately one half of the area of the substrate 480 of the tip 478, and the shielding material 488 covers approximately the other one half of the area. This configuration generates a generally hemispherical therapeutic X-ray beam field 492. It should be appreciated that the invention is not limited in this regard. The target material 484 and the corresponding amount of shielding 488 can respectively be more or less than one-half, for example the target can be one-quarter and the shielding can be three-quarters of the area of the substrate 480, or vice versa. The position of the target material in the tip 478 can also be varied, and the target material 484 can have many different sizes, locations and geometries. The electron beam 490 can be steered to strike the target material 484 wherever it is located, and by varying the location, size, shape of the target material 484 and the direction and beam energy of the electron beam 490, the location, size, three dimensional shape and dose delivered by resulting X-ray beam field can be controlled.

Figure 19:
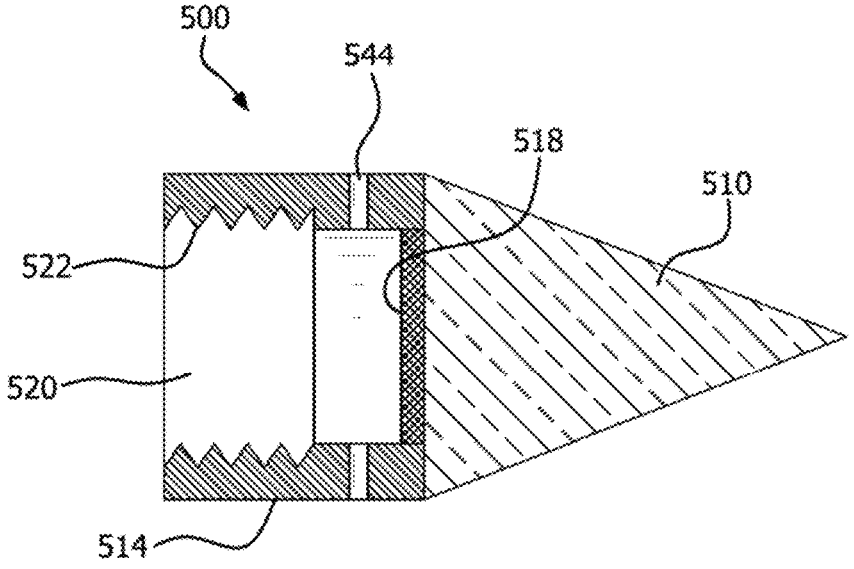
FIG. 19 is a schematic cross section of a removable tip for a radiosurgical needle.
Figure 20:
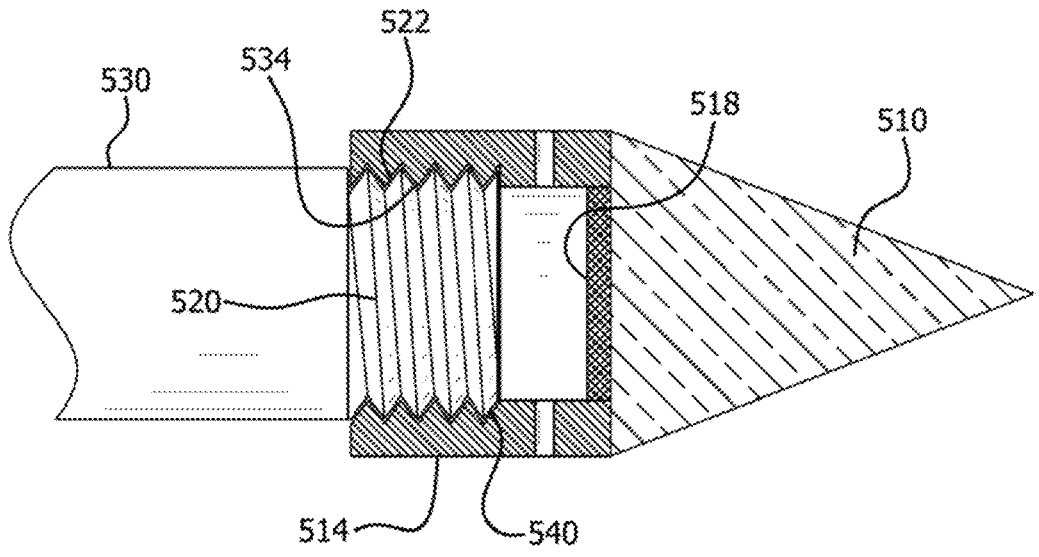
FIG. 20 is a side elevation, partially broken away and partially in cross section, of a radiosurgical needle with the removable tip of FIG. 19.

There is shown in FIGS. 19-20 a detachable tip assembly 500 for the radiosurgical needle 530. In this embodiment, the detachable tip assembly 500 has a pointed radiolucent tip 510 and sidewalls 514 which can be radiolucent or radiopaque. A target material 518 is positioned within an open interior 520 defined by the sidewalls 514. Threads 522 can be provided for engaging the needle body 530. Cooperating threads 540 can be provided on the needle body 530 to permit ready replacement of the detachable tip assembly 500. The sidewalls 514 and pointed tip 510 can be made of the same material or a different material and connected by suitable welds or brazing 544.

Figure 21:
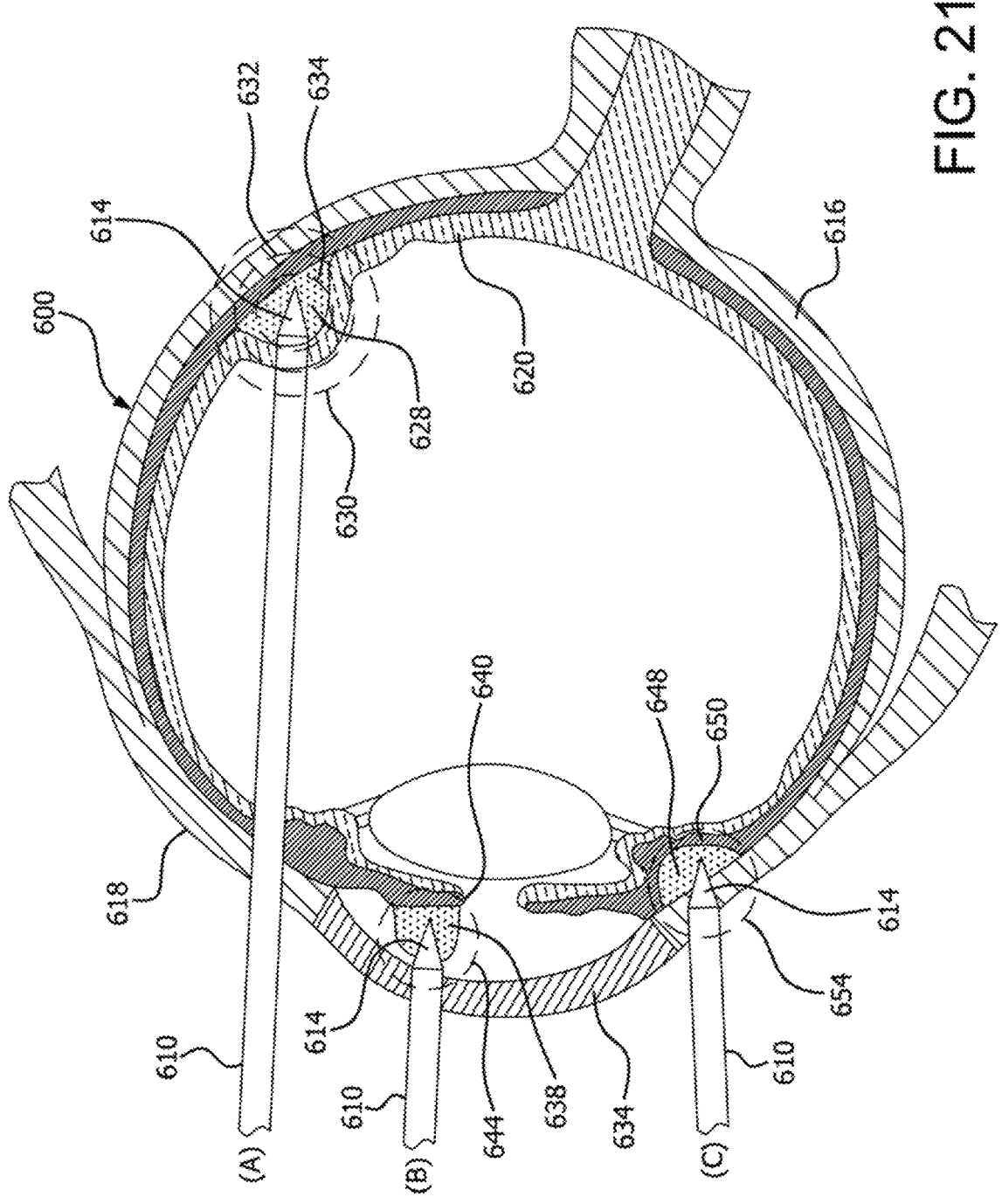
FIG. 21 is a cross section of an eye illustrating the treatment of tumors in various locations within the eye by an embodiment of the invention.

There is shown in FIG. 21 an embodiment of the invention for treatment of an eye 600. A radiosurgical needle 610 has a tip 614. The radiosurgical needle 610 is inserted into the eye 600 using the pointed tip 614 to puncture tissue of the eye 600 such as the sclera 616 or the ciliary body 618. As shown in example (A), the radiosurgical needle 610 is advanced to the retina 620 and a tumor 628 of or adjacent to the retina 620. The radiosurgical needle 610 is then energized to emit an X-ray beam field 630. The size of the X-ray beam field can be enlarged or reduced by varying the energy of the electron beam passing through the radiosurgical needle 610. For example, by reducing the electron beam energy a smaller X-ray beam field 632 can be produced and with further reductions of the electron beam energy a still smaller electric X-ray beam field 634 can be produced.

There is also shown in FIG. 21 an embodiment (B) in which a tumor 638 is located on the iris 640. In this case, the tip 614 of the radiosurgical needle 610 is inserted through the cornea 634 and energized to generate a therapeutic X-ray beam field 644. Also shown in FIG. 21 is an embodiment in which a tumor 648 is located adjacent the ciliary muscle 650. The radiosurgical needle 610 is advanced such that the tip 614 is adjacent or enters the tumor 648. The radiosurgical needle 610 is energized to generate a therapeutic X-ray beam field 654 which will treat the tumor 648. The size and dose of the therapeutic X-ray beam field can be adjusted by adjusting the energy of the electron beam passing through the radiosurgical needle 610.

Figure 22:
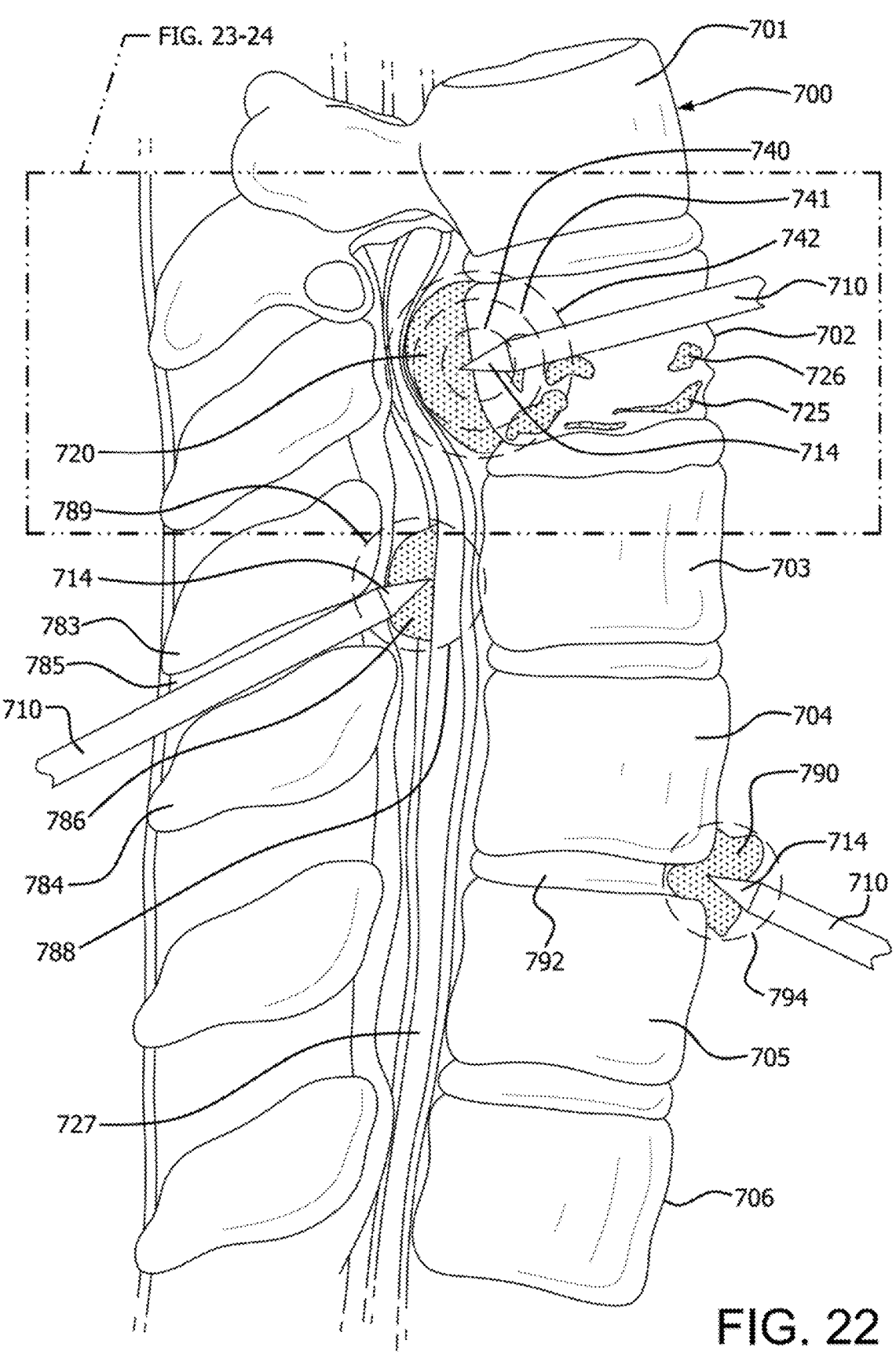
FIG. 22 is a side elevation of a portion of a spine illustrating the treatment of tumors in various locations of the spine by an embodiment of the invention.
Figure 23:
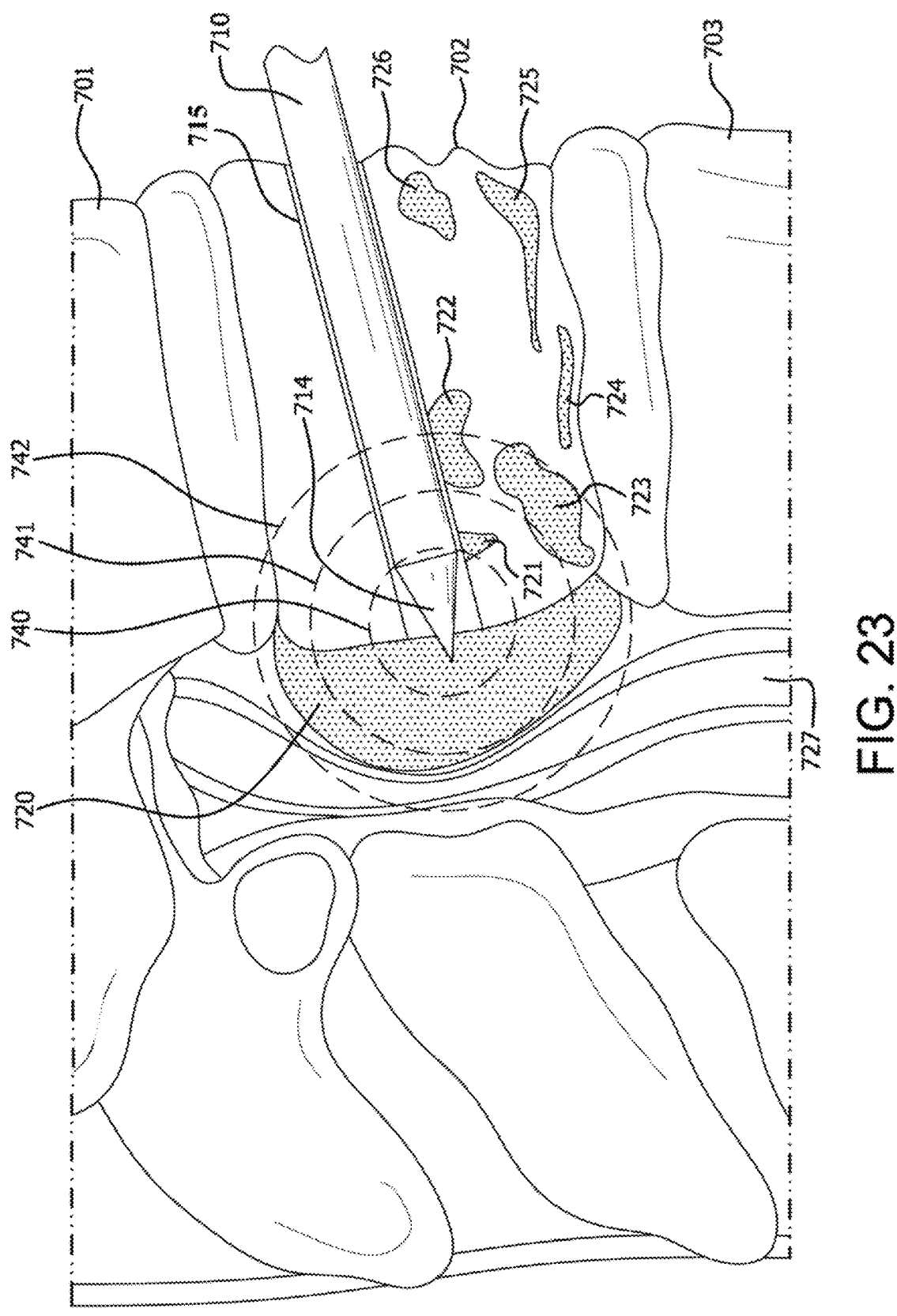
FIG. 23 is an expanded view of area FIG. 23-24 in FIG. 22, in a first mode of operation.
Figure 24:
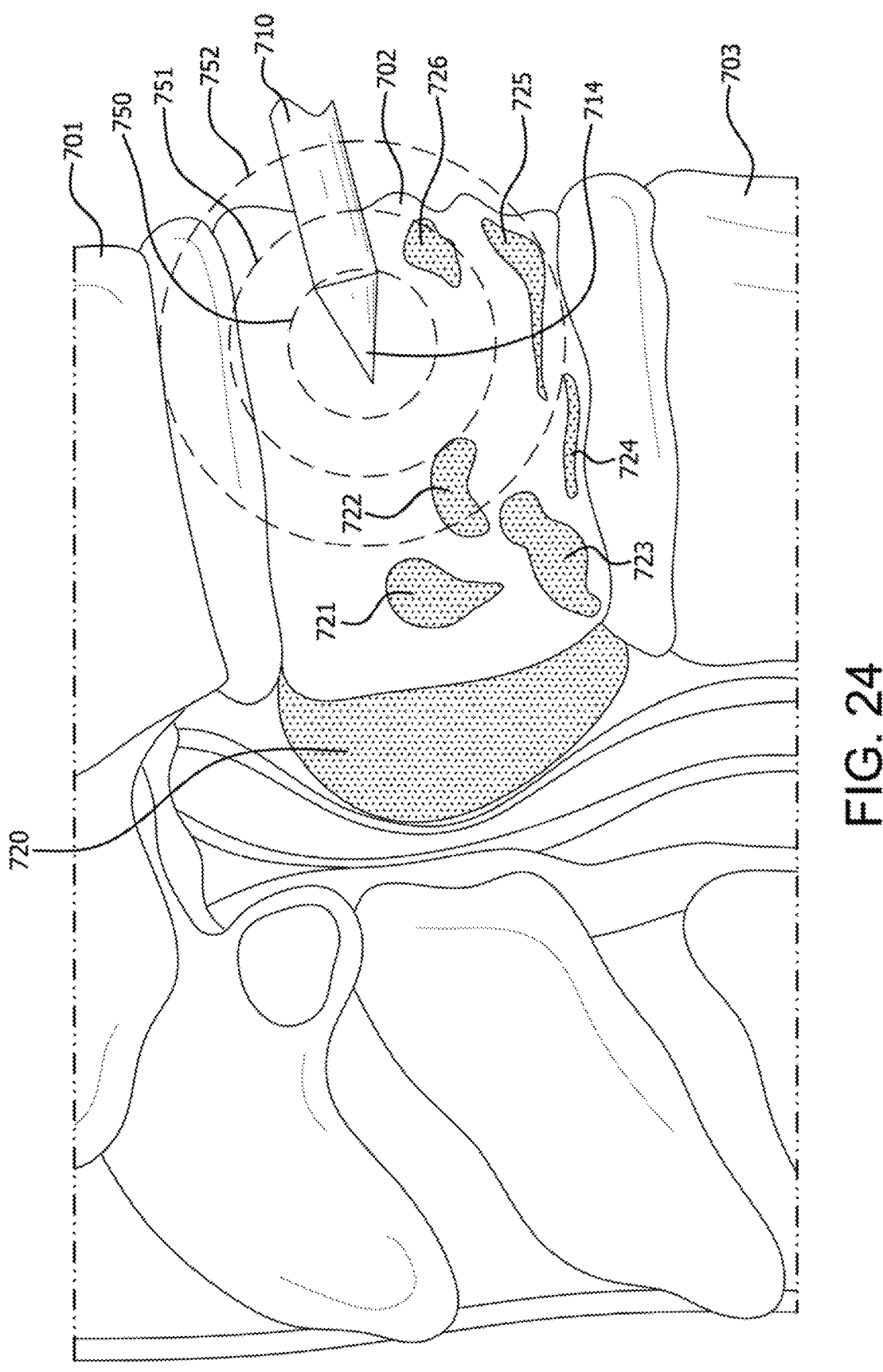
FIG. 24 is an expanded view of area FIG. 23-24 in FIG. 22, in a second mode of operation.

There is shown in FIGS. 22-24 a section of a spine 700. The section of the spine 700 includes vertebrae 701-706. In this example, the patient has a number of tumors 720-726 that are localized within and about the vertebrae 702 including a tumor 720 that is located adjacent to the spinal cord 727. A radiosurgical needle 710 having a tip 714 is advanced through an intervertebral space or a bore 715 (FIG. 23) that can be formed with a surgical drill to allow for the passage of the radiosurgical needle 710. The tip 714 of the radiosurgical needle 710 is positioned in or adjacent to the tumor 720. The radiosurgical needle 710 is then energized to generate a therapeutic X-ray beam field 740. The energy of the electron beam can be raised or lowered to increase or decrease the size and dose of the therapeutic X-ray beam field, such that a therapeutic X-ray beam field 741 of larger dimension than the therapeutic X-ray beam field 740 can be created. The application of more electron beam energy a still larger therapeutic X-ray being field 742 can be created according to the treatment plan for the patient, as shown in FIG. 23. The radiosurgical needle 710 can be withdrawn a distance and repositioned so as to generate therapeutic X-ray beam fields which will treat others of the tumors 721-726, as shown in FIG. 24. The size and dose of the therapeutic X-ray beam field 750 in this example can be increased to create a larger and more intense therapeutic X-ray beam filled 751, or a still larger and more intense therapeutic X-ray beam field 752.

The radiosurgical needle 710 can be used to treat tumors in other locations of the spine 700. A tumor 786 is located adjacent the spinal cord 727 and is positioned between the spinous processes 783 and 784 of the vertebrae 703, 704 (FIG. 22). The radiosurgical needle 710 can be positioned through the space 785 between the spinous processes 783 and 784 such that the tip 714 is positioned in or near the tumor 786. The radiosurgical needle 710 is energized to generate a therapeutic X-ray beam field 789 to treat the tumor 786.

In another embodiment shown in FIG. 22, a tumor 790 is located at the intervertebral space between vertebrae 704 and 705, and adjacent the intervertebral disk 792. The radiosurgical needle 710 can be inserted anteriorly and with the tip 714 in or adjacent to the tumor 790. The radiosurgical needle 710 is energized by an electron beam to generate a therapeutic X-ray beam field 794. The energy of the electron beam can varied to vary the size and dose of the therapeutic X-ray beam field.

Figure 25:
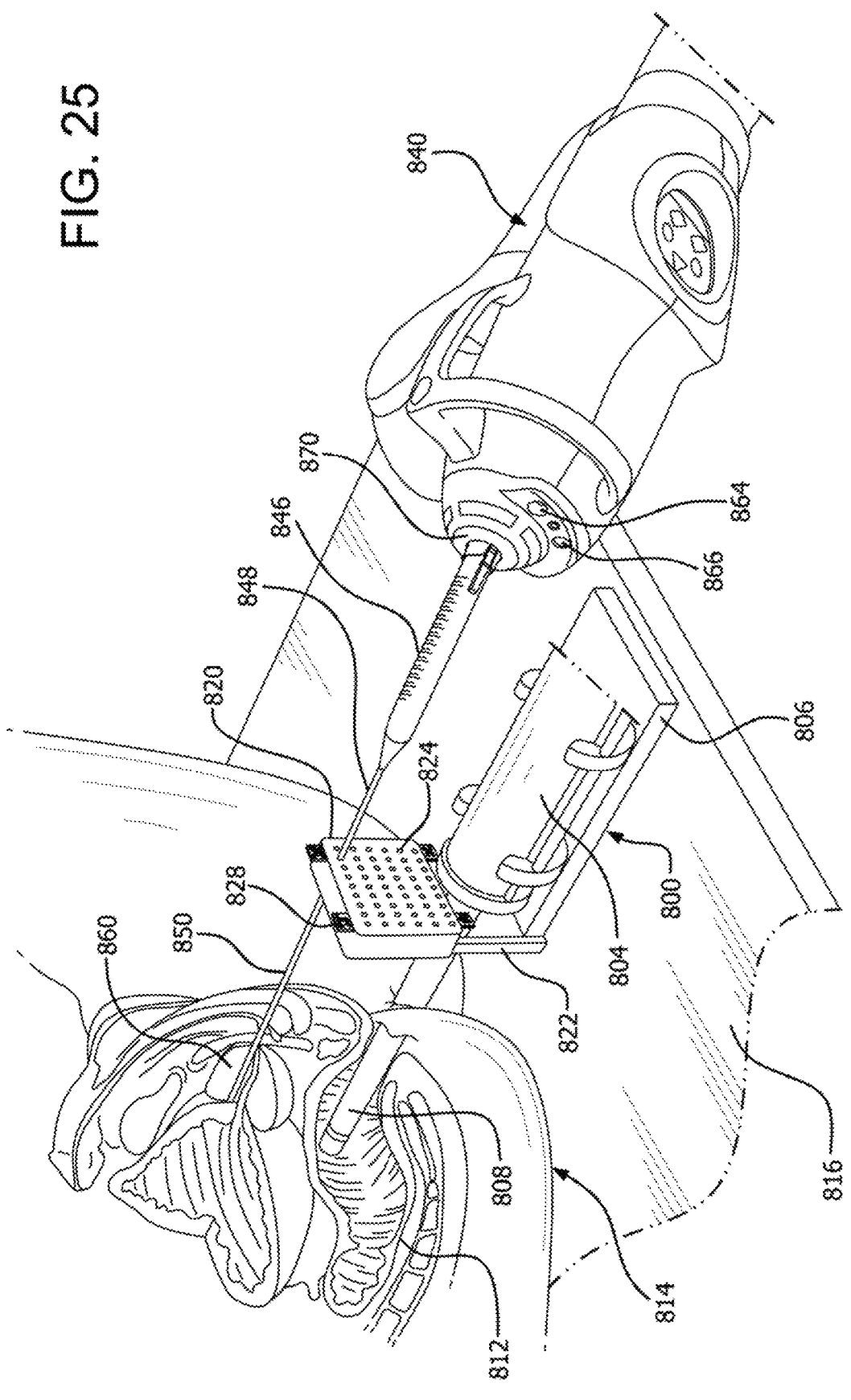
FIG. 25 is a perspective view of an embodiment incorporating image guided alignment.
Figure 26:
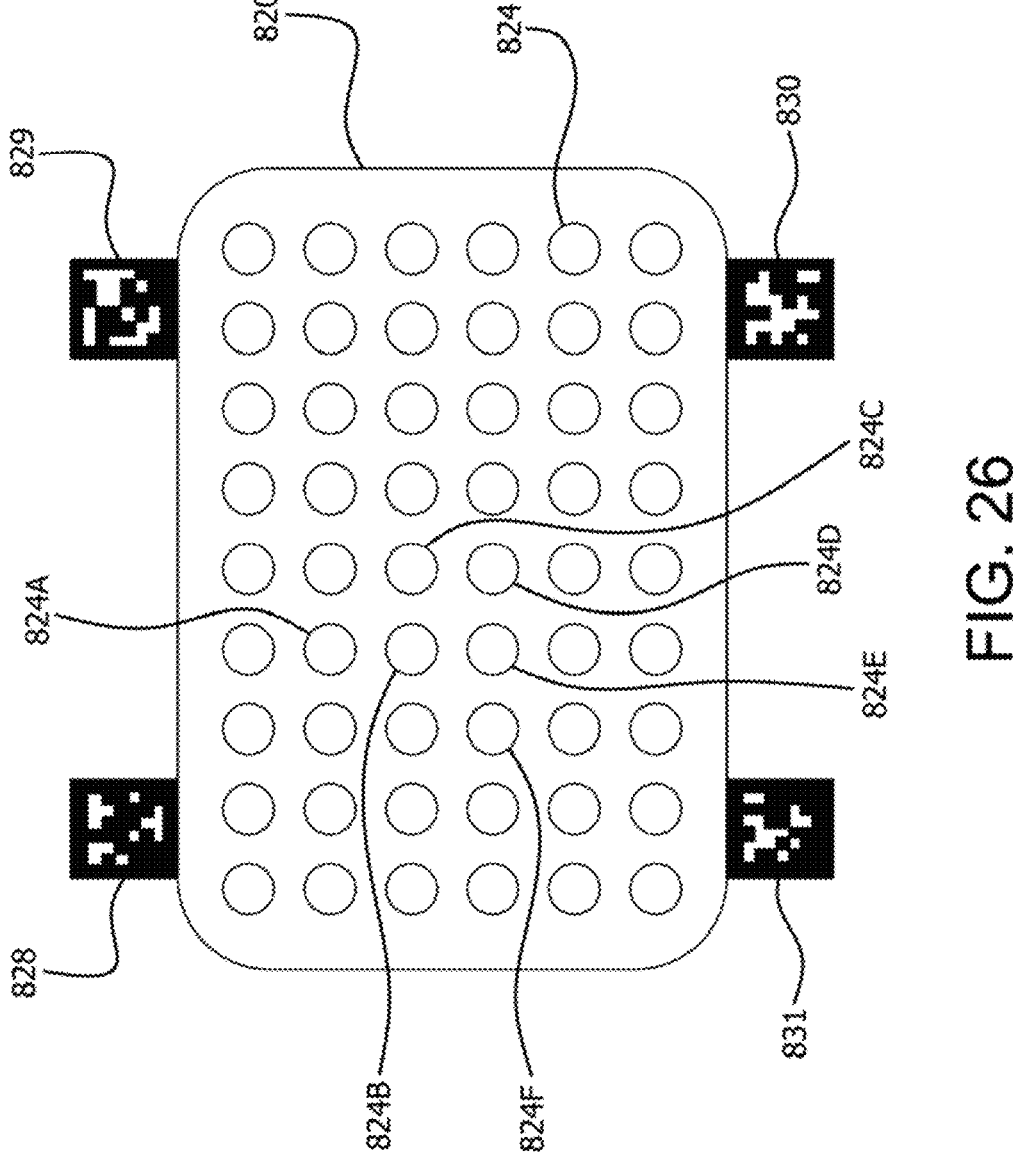
FIG. 26 is a plan view of a guidance device for a radiosurgical needle system for use with image guidance.

There is shown in FIGS. 25-26 a guidance module 800 for a radiosurgical needle 850. The guidance module 800 can include an ultrasound device 804 which can include an ultrasound transducer 808. The ultrasound transducer 808 is dimensioned for insertion into the anus 812 or other location of the patient 814. The guidance module 800 includes a guidance device 820 with April code such as Apriltags 828-831 or other spatial orientation tags for robotic machine vision head guidance. The spatial orientation tags 828-831 can vary in number, location and type. The physical position of the spatial orientation tags 828-831 is determined by a suitable machine vision device such as a camera and interpreted by the treatment planning software. The physical position of the spatial orientation tags is used along with readings from the ultrasound transducer 808 to orient and align the radiosurgical needle 850 to the treatment geometry. The head unit 840 can have one or more machine vision cameras 864 and 866 for identifying the Apriltags 828-831 and thereby the position in space of the guidance device 820.

The guidance module 800 can include a guidance support 806. The patient 814 can be supported by supporting table 816. The guidance support 806 can have many different shapes and sizes and can be secured to the table 816, to structure secured to the table 816, to a separate supporting structure not part of the table 816, or to a portion of a base unit (not shown) supporting the radiosurgical head unit 840, similar to the base unit 18 in FIG. 1.

The guidance device 820 is mounted by suitable structure to the guidance module 800, for example to the guidance support 806 by supporting arms 822 or other suitable structure that are part of the guidance module 800. The ultrasound device 804 can also be mounted to the guidance module 800, for example to the guidance support 806. The position of the guidance device 820 and thereby the spatial orientation tags 828-831 will thereby be fixed relative to the position of the ultrasound transducer 808. The radiosurgical needle 850 can be properly located by the treatment planning software relative to the transducer 808 and thereby directed to the tissue to be treated.

In operation, the ultrasound transducer 808 is inserted into the anus 812 of the patient 814 or other orifice such as the vagina and is used to determine the position of the target tissue such as a tumor in the prostate 860. The ultrasound transducer 808 surveys the desired portion of the patient such as the prostate 860 and returns this information for processing by the treatment planning system.

The radiosurgical needle 850 is advanced by movement of the radiosurgical head unit 840 as by a robotic arm. This movement is directed by the treatment planning system according to the position of the radiosurgical needle 850 relative to the spatial orientation tags as seen by the machine vision cameras 864 and 866, and the output of the ultrasound device 804. The radiosurgical needle 850 is guided to the tumor by the machine vision software and treatment planning system using this information. An illuminating light such as LED ring 870 can facilitate the machine vision. The radiosurgical needle 850 is then activated to deliver radiation therapy to the prostate 860 in the location of a tumor or other abnormality being treated. The radiosurgical head unit 840 has a drift tube 846 joined to the distal end 848 of radiosurgical needle 850 to supply the directed electron beam to the radiosurgical needle 850 and generate a therapeutic x-ray beam field.

The guidance device 820 can also include a plurality of guidance apertures 824 which serve to position, guide and stabilize the radiosurgical needle 850 during the treatment process. The treatment plan may dictate that the radiosurgical needle 850 be advanced through guidance aperture 824A and advanced to a particular depth in the patient 814 (FIG. 26). The radiosurgical needle 850 is then withdrawn, and using the machine vision, directed through the next guidance aperture 824B to a depth within the patient determined by the treatment plan. The process is continued for example through guidance apertures 824C, 824D, 824E, and 824F until the tumor or other target tissue has been radiated according to the treatment plan. In this manner the tumor can be thoroughly irradiated despite having varying contours and depths.

The invention as shown in the drawings and described in detail herein disclose arrangements of elements of particular construction and configuration for illustrating preferred embodiments of structure and method of operation of the present invention. It is to be understood however, that elements of different construction and configuration and other arrangements thereof, other than those illustrated and described may be employed in accordance with the spirit of the invention, and such changes, alternations and modifications as would occur to those skilled in the art are considered to be within the scope of this invention as broadly defined in the appended claims. In addition, it is to be understood that the phraseology and terminology employed herein are for the purpose of description and should not be regarded as limiting.

We claim:

1. A radiotherapy system, comprising:
an electron source for generating an initial electron beam;
a first beam corrector for focusing the initial electron beam into a focused electron beam;
a Bremsstrahlung target comprising target material that when impacted by the focused electron beam generates Bremsstrahlung x-ray photons;
a radiosurgical needle with an elongated radiopaque needle body portion having an interior lumen, a proximal end and a distal end, the distal end comprising a pointed tissue-piercing tip for piercing a tissue of a patient, wherein the elongated radiopaque needle body portion of the radiosurgical needle has an outside diameter and the pointed tissue-piercing tip has a smallest tip diameter, and the smallest tip diameter is less than the outside diameter of the elongated radiopaque needle body portion, the target being positioned within the lumen of the radiosurgical needle and closer to the distal end than the proximal end;
a radiolucent portion for transmitting x-ray photons generated at the Bremsstrahlung target to surrounding tissue, wherein the Bremsstrahlung target, the radiolucent portion, and the pointed tip are provided at the distal end of the radiosurgical needle, and the Bremsstrahlung target and radiolucent portion are geometrically positionable for beam forming and targeting towards tissues being treated;
an elongated radiopaque micro drift tube with an open interior extending from the electron source to the radiosurgical needle, the micro drift tube having a proximal end nearest the electron source, and a distal end nearest the radiosurgical needle, the proximal end of the radiosurgical needle being affixed to the distal end of the micro drift tube, the open interior of the micro drift tube communicating with the lumen of the radiosurgical needle so as to define an electron flow path from the electron source to the Bremsstrahlung target; and,
a first beam steering device for steering the focused electron beam within the micro drift tube to the Bremsstrahlung target.

2. The radiotherapy system of claim 1, wherein the distal end of the radiosurgical needle comprises a radiolucent portion for transmitting x-ray photons generated at the Bremsstrahlung target.

3. The radiotherapy system of claim 1, further comprising a vacuum connection for connecting to a vacuum source for maintaining a vacuum within the open interior of the micro drift tube and the lumen of the radiosurgical needle.

4. The radiotherapy system of claim 1, wherein the open interior of the micro drift tube has a diameter of from 1 to 5 mm.

5. The radiotherapy system of claim 1, wherein the interior lumen of the radiosurgical needle has a diameter of between 1 and 5 mm.

6. The radiotherapy system of claim 1, wherein the elongated radiopaque needle body portion of the radiosurgical needle has an outside diameter of from 1 to 5 mm.

7. The radiotherapy system of claim 1, wherein the pointed tissue-piercing tip comprises an open space defined by interior tip walls, wherein the target material is affixed to the interior tip walls, and wherein the open space of the pointed tip communicates with the lumen of the radiosurgical needle to permit the focused electron beam to strike the target material affixed to the interior tip walls.

8. The radiotherapy system of claim 1, wherein the target material is provided proximal to the pointed tip.

9. The radiotherapy system of claim 1, wherein the target material spans the lumen of the radiosurgical needle.

10. The radiotherapy system of claim 1, wherein the radiolucent portion of the radiosurgical needle is provided in the pointed tip, wherein x-ray photons generated at the target material will be transmitted through the pointed tip.

11. The radiotherapy system of claim 1, wherein the radiolucent portion of the radiosurgical needle is provided proximal to the target material so as to transmit x-ray photons proximal to the target material.

12. The radiotherapy system of claim 1, wherein the target material comprises at least one selected from the group consisting of molybdenum, tungsten and gold.

13. The radiotherapy system of claim 12, wherein the target material is disposed on a substrate.

14. The radiotherapy system of claim 13, wherein the substrate comprises at least one selected from the group consisting of beryllium, aluminum, sapphire, diamond, alumina, and boron nitride.

15. The radiotherapy system of claim 1, wherein the radiolucent portion comprises silicon carbide.

16. The radiotherapy system of claim 1, further comprising a robotic support for moving the radiosurgical needle to a treatment location within a patient, and for withdrawing the radiosurgical needle from the treatment location.

17. The radiotherapy system of claim 16, further comprising a processor for receiving treatment planning data and patient position data, and for processing the treatment planning data and the patient position data to move the radiosurgical needle to a treatment location within the patient and to cause the electron source, the beam corrector and the beam steering device to direct the beam to a target with a beam energy and for a duration according to the treatment plan.

18. The radiotherapy system of claim 16, wherein the electron source, beam corrector, first beam steering device, micro drift tube, and radiosurgical needle are provided in a treatment head, the treatment head being connected to the robotic support.

19. The radiotherapy system of claim 16, wherein the robotic support comprises a robotic arm capable of three-dimensional movement.

20. The radiotherapy system of claim 1, further comprising a guidance module comprising a guidance device with spatial orientation tags.

21. The radiotherapy system of claim 20, wherein the guidance device is mounted to a guidance support.

22. The radiotherapy system of claim 21, further comprising an ultrasound device mounted to the guidance support.

23. The radiotherapy system of claim 22, wherein the guidance device comprises apertures dimensioned to receive the radiosurgical needle.

24. The radiotherapy system of claim 1, further comprising a second beam corrector, the second beam corrector being distal to the first beam corrector and the first beam steering device, and closer to the proximal end of the radiosurgical needle than the first beam corrector, the second beam corrector acting on the focused electron beam to produce a refocused electron beam at a distal end of the micro drift tube.

25. The radiotherapy system of claim 24, further comprising a second beam steering device, the second beam steering device being distal to the first beam corrector and the first beam steering device, and closer to the proximal end of the radiosurgical needle than the first beam steering device, the second beam steering device steering the refocused electron beam to the Bremsstrahlung target.

26. A radiotherapy system, comprising:

I. a treatment head comprising:

an electron source for generating an initial electron beam;

a first beam corrector for focusing the initial electron beam into a focused electron beam;

a Bremsstrahlung target comprising target material that when impacted by the focused electron beam, generates Bremsstrahlung x-ray photons;

a radiosurgical needle with an elongated radiopaque needle body portion having an interior lumen, a proximal end and a distal end, the distal end comprising a pointed tissue-piercing tip, wherein the elongated radiopaque needle body portion of the radiosurgical needle has an outside diameter and the pointed tissue-piercing tip has a smallest tip diameter, and the smallest tip diameter is less than the outside diameter of the elongated radiopaque needle body portion, the Bremsstrahlung target being positioned within the lumen and closer to the distal end than the proximal end, the distal end of the radiosurgical needle comprising a radiolucent portion for transmitting x-ray photons generated at the Bremsstrahlung target to surrounding tissues, the radiosurgical needle further comprising a pointed tip portion for piercing a tissue of a patient, wherein the Bremsstrahlung target, the radiolucent portion, and the pointed tip are provided at the distal end of the radiosurgical needle, and the Bremsstrahlung target and radiolucent portion are geometrically positionable for beam forming and targeting towards tissues being treated;

a first beam steering device for steering the focused electron beam to the target; and, an elongated radiopaque micro drift tube with an open interior extending from the electron source to the radiosurgical needle, the micro drift tube having a proximal end nearest the electron source, and a distal end nearest the radiosurgical needle, the proximal end of the radiosurgical needle being affixed to the distal end of the micro drift tube, the open interior of the micro drift tube communicating with the lumen of the radiosurgical needle so as to define an electron flow path from the electron source to the Bremsstrahlung target;

II. a robotic arm for manipulating the treatment head; and,

III. a base unit for supporting the robotic arm.

27. A method for conducting radiotherapy, comprising the steps of:

providing a radiosurgical needle with an elongated radiopaque needle body portion having an interior lumen, a proximal end and a distal end, the distal end comprising a pointed tissue-piercing tip for piercing the tissue of a patient, wherein the elongated radiopaque needle body portion of the radiosurgical needle has an outside diameter and the pointed tip has a tip diameter, and the tip diameter is less than the outside diameter of the elongated radiopaque needle body portion, the radiosurgical needle further comprising a Bremsstrahlung target comprising target material that when impacted by the focused electron beam generates Bremsstrahlung x-ray photons, the Bremsstrahlung target being positioned within the lumen, the radiosurgical needle comprising a radiolucent portion for transmitting x-ray photons generated at the target to surrounding tissues, wherein the target, the radiolucent portion, and the pointed tip are provided at the distal end of the radiosurgical needle, and the Bremsstrahlung target and radiolucent portion are geometrically positionable for beam forming and targeting towards tissues being treated;

inserting the radiosurgical needle into the body of a patient by piercing a tissue of the patient with the tissue-piercing tip and advancing the radiosurgical needle to a patient therapy location;

directing a focused and steered electron beam at the target, wherein Bremsstrahlung x-ray photons will be generated at the target and will be transmitted through the radiolucent portion to the patient therapy location.

28. The method of claim 27, wherein the patient therapy location comprises a tumor in a prostate.

29. The method of claim 27, wherein the patient therapy location comprises a tumor in an eye.

30. The method of claim 27, wherein the patient therapy location comprises a tumor of the spine.

31. The radiotherapy system of claim 1, wherein the pointed tip of the radiosurgical needle has a diameter of from 10-1000 microns.

32. The radiotherapy system of claim 1, wherein the pointed tip of the radiosurgical needle has a diameter of from 10-3350 microns and the elongated radiopaque needle body portion of the radiosurgical needle has an outside diameter of from 1 to 5 mm.

33. The radiotherapy system of claim 26, wherein the pointed tissue-piercing tip of the radiosurgical needle has a tip diameter of from 10-3350 microns and the elongated radiopaque needle body portion of the radiosurgical needle has an outside diameter of from 1 to 5 mm.

34. The radiotherapy system of claim 26, wherein the pointed tissue-piercing tip of the radiosurgical needle has a tip diameter of from 10-1000 microns.

35. The method of claim 27, wherein the pointed tissue-piercing tip of the radiosurgical needle has a tip diameter of from 10-3350 microns and the elongated radiopaque needle body portion of the radiosurgical needle has an outside diameter of from 1 to 5 mm.

36. The method of claim 27, wherein the pointed tissue-piercing tip of the radiosurgical needle has a tip diameter of from 10-1000 microns.

\* \* \* \* \*